United States Patent [19]

MacKay et al.

[11] Patent Number: 5,135,854
[45] Date of Patent: Aug. 4, 1992

[54] METHODS OF REGULATING PROTEIN GLYCOSYLATION

[75] Inventors: Vivian L. MacKay; Susan K. Welch, both of Seattle; Carli L. Yip, Bellevue, all of Wash.

[73] Assignee: ZymoGenetics, Inc., Seattle, Wash.

[21] Appl. No.: 189,547

[22] Filed: May 3, 1988

Related U.S. Application Data

[63] Continuation-in-part of Ser. No. 116,095, Oct. 29, 1987, abandoned.

[51] Int. Cl.$^5$ .................... C12N 15/00; C12N 15/81; C12N 1/19; C12P 21/02
[52] U.S. Cl. .................... 435/69.1; 435/69.2; 435/69.6; 435/255; 435/256; 935/50; 935/69
[58] Field of Search .................... 435/69.1–69.9, 435/214, 215, 212, 217, 255, 256, 320, 172.3, 942; 935/50, 69

[56] References Cited

U.S. PATENT DOCUMENTS 4,620,948 11/1986 Builder et al. .................... 435/69.1 X

FOREIGN PATENT DOCUMENTS 0171142 2/1986 European Pat. Off. ........... 435/69.1

OTHER PUBLICATIONS

Moir, D. T., et al. 1987. *Gene* vol. 56, pp. 209–217.
Ballou, L., et al. 1980. *Journal of Biological Chemistry* vol. 255, pp. 5986–5991.
Werner-Washburne, M., et al. 1987. *Molecular and Cellular Biology* vol. 7 pp. 2568–2577.
Tsai, P. K., et al. 1984. *Journal of Biological Chemistry* vol. 259 pp. 3805–3811.
Brand, A. H., et al. 1985. *Cell* vol. 41 pp. 41–48.
Rine, J., et al. 1987. *Genetics* vol. 116 pp. 9–22.
Kukuruzinska, M. A., et al. *Annual Reviews of Biochemistry* vol. 56 pp. 915–944.

*Primary Examiner*—Richard A. Schwartz
*Assistant Examiner*—Mary E. Mosher
*Attorney, Agent, or Firm*—Seed and Berry

[57] ABSTRACT

Methods for producing a heterologous protein or polypeptide are disclosed. A preferred method utilizes a fungal cell carrying a defect in a gene whose product is required for the addition of outer chain oligosaccharide moieties to glycoproteins, the cell transformed with a first DNA construct comprising a regulated promoter followed downstream by a DNA sequence which complements the defect, and a second DNA construct comprising a second promoter followed downstream by a DNA sequence encoding a secretion signal and a DNA sequence encoding a heterologous protein or polypeptide. A yeast cell having a Mnn9$^-$ phenotype and capable of producing colonies of normal morphologies in the absence of osmotic stabilization is also disclosed.

30 Claims, 8 Drawing Sheets

Figure 1
A. <u>mnn9</u> oligosaccharide
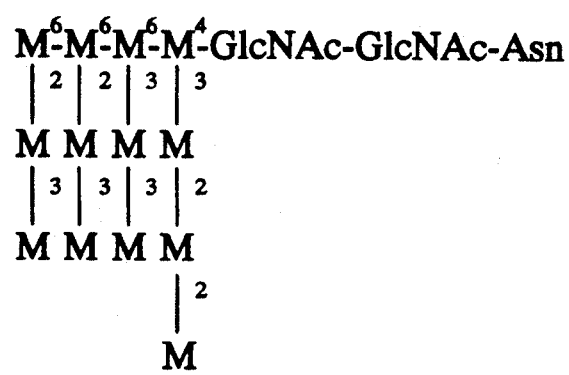
B. <u>mnn1</u> <u>mnn9</u> oligosaccharide
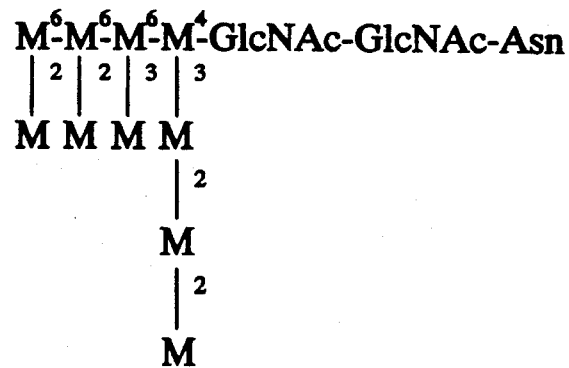

Figure 4

```
                                              -140      -130      -120
                                AAGCTTTTATTATTTCTGTAGCCGCTCTTGGGACCCGTTA

-110       -100        -90        -80        -70        -60        -50        -40        -30        -20        -10
TTCTGAACCTATTTTCCTTCCGCACTTTGTGAAGTAAGAGAGAATAGCATCAATTTAGTATTTTCAAACAGAAGAATTAAAAGAGCTAGAATAAAAGTTAGGAAACA

+1                    10              20              30              40              50              60              70              80
    ATG TCA CTT TCT CTT GTA TCG TAC CGC CTA AGA AAG AAC CCG GTT AAC ATT TTT CTA CCT GTT TTG GCC ATA TTT CTA ATA TAT
    Met Ser Leu Ser Leu Val Ser Tyr Arg Leu Arg Lys Asn Pro Val Asn Ile Phe Leu Pro Val Leu Ala Ile Phe Leu Ile Tyr 90             100             110             120             130             140             150             160             170
    ATA ATT TTT TTC CAG AGA GAT TCT CTG TTG GGA CTT AAT GGC CAG TCC ATT CAA CAC AAA TGG GCA CAC GAA AAG GAA AAC
    Ile Ile Phe Phe Gln Arg Asp Ser Leu Leu Gly Leu Asn Gly Gln Ser Ile Gln His Lys Trp Ala His Glu Lys Glu Asn 180             190             200             210             220             230             240             250             260
    ACA TTT TAT TTT CCC TTC ACC AAG TAC AAA ATG CCA AAG TAC TCT TAT AAG TAT CTG AAG TCA AGC GGC TGG TTG TTC AAC GAT CAC GTG
    Thr Phe Tyr Phe Pro Phe Thr Lys Tyr Lys Met Pro Lys Tyr Ser Tyr Lys Tyr Leu Lys Ser Gly Trp Leu Phe Asn Asp His Val 270             280             290             300             310             320             330             340
    GAA GAT ATT ATC CCA GAA GGT CAT TAT GCA CAT ATT GCA CTC TCT ACG TCA GAA GCA GCT GTC AAT AAG AAG GAG CAT
    Glu Asp Ile Ile Pro Glu Gly His Tyr Ala His Ile Ala Leu Ser Thr Ser Glu Ala Ala Val Asn Lys Lys Glu His

Pst I 410
        360             370             380             390         400            420             430
    ATT TTG ATA TTG ACT CCA AGA ACA ATG CAA TTT CAT CAA CAC TTT TTG CTG CAG AAT TAC CTA AAT TAC CCT CGG GAA TTG ATT GAA
    Ile Leu Ile Leu Thr Pro Arg Thr Met Gln Phe His Gln His Phe Leu Leu Gln Asn Tyr Leu Asn Tyr Pro Arg Glu Leu Ile Glu 440             450             460             470             480             490             500             510             520
    TTG GGG TTC ATT ACA CCA AGA ACA GCC ACT GGT GAC TTG GCC TTA AAG AAA TTG GAG AAT GCT ATT AAA AAG TTA CAA ACG GAC AAG
    Leu Gly Phe Ile Thr Pro Arg Thr Ala Thr Gly Asp Leu Ala Leu Lys Lys Leu Glu Asn Ala Ile Lys Lys Leu Gln Thr Asp Lys 530             540             550             560             570             580             590             600
    AAA ACT CAA AGA TTT AGT AAA ATT ACT ATT TTG CGA CAG AGT TTT GAT AAG TTG ATG GAG AAG GAA AGA CAC GCT TTA
    Lys Thr Gln Arg Phe Ser Lys Ile Thr Ile Leu Arg Gln Ser Phe Asp Lys Leu Met Glu Lys Glu Arg His Ala Leu
```

Figure 4a

```
     620         630         640         650         660         670         680         690
GAT GTT CAA AAG GAA AGA CGT GCA GCA ATG GCT TTG GCG AAT GAA TTA CTA TTC TCC ACC ATA GGA CCT CAC ACT TCT TGG GTG
Asp Val Gln Lys Glu Arg Arg Ala Ala Met Ala Leu Ala Arg Asn Glu Leu Leu Phe Ser Thr Ile Gly Pro His Thr Ser Trp Val 700         710         720         730         740         750         760         770         780
CTG TGG CTA GAT GCC GAT ATT ATA GAG ACA CCA TCT TTA ATT CAA GAC ATG ACC AAA CAC AAC AAA GCT ATC TTA GCT GCA AAC
Leu Trp Leu Asp Ala Asp Ile Ile Glu Thr Pro Pro Ser Leu Ile Gln Asp Met Thr Lys His Asn Lys Ala Ile Leu Ala Ala Asn 790         800         810         820         830         840         850         860         870
ATT TAT CAA AGA TTT TAC GAT GAA GAG AAG AAG GTG CTG AAG CAA CCA TCA ATC AGA CCA TAC GAT TTC AAC AAC TGG CAA GAA AGT GAC ACC GGT
Ile Tyr Gln Arg Phe Tyr Asp Glu Glu Lys Lys Val Leu Lys Gln Pro Ser Ile Arg Pro Tyr Asp Phe Asn Asn Trp Gln Glu Ser Asp Thr Gly 880         890         900         910         920         930         940         950
TTA GAA ATA GCC TCT CAG ATG GAT GAC GAG ATT ATT GTC GAG GGT TAT GCA GAA ATT GCC ACT TAT AGG CCA CTA ATG GCT CAT
Leu Glu Ile Ala Ser Gln Met Asp Asp Glu Ile Ile Val Glu Gly Tyr Ala Glu Ile Ala Thr Tyr Arg Pro Leu Met Ala His 960         970         980         990        1000        1010        1020        1030        1040
TTC TAC GAT GCT AAT GGC GTA CCA GGT GAA GAG ATG GCG GGC ATG GGT GGT GAT GGT GTT ACT TTG GTC AAA GCA GAA GTT CAC
Phe Tyr Asp Ala Asn Gly Val Pro Gly Glu Glu Met Ala Gly Met Gly Gly Asp Gly Val Gly Gly Cys Thr Leu Val Lys Ala Glu Val His 1050        1060        1070        1080        1090        1100        1110        1120        1130
AGA GAC GGT GCC ATG TTC CCT AAT TTC TAT CAC TTG CCA TTT ATT GAA ACA GAA GGT TTT GCT AAG ATG GCG AAG AGA TTA AAC TAC
Arg Asp Gly Ala Met Phe Pro Asn Phe Tyr His Leu Pro Phe Ile Glu Thr Glu Gly Phe Ala Lys Met Ala Lys Arg Leu Asn Tyr 1140        1150        1160        1170        1180        1190        1200        1210        1220
GAT GTA TTT GGC TTA CCA AAC TAT TTG GTT TAT CAC ATA GAG GAA GAG AAC CAT TGA GCAACTGAGCAAAAGCATACAGAGAAGCTATAGCGTTATT
Asp Val Phe Gly Leu Pro Asn Tyr Leu Val Tyr His Ile Glu Glu Glu Asn His 1240        1250        1260        1270        1280        1290        1300        1310        1320        1330        1340
GAAAGATAATATATTGTTGCGATTATTAGTTGAAAATAAACAAACAAGATAATTCATATATAATTCATATATATTAAAAATGCCGAATAAAAAGTGCT 1350        1360        1370        1380        1390        1400        1410        1420        1430        1440        1450
ACAACAACTAATTCTGAGCTTGAGAATAACCATTCACATTTATTCTTTATCATTTATAAATCGGTGGTCTTGACTTTTATTCCTTTCTAGTCTAACAA 1470        1480        1490        1500        1510        1520        1530        1540        1550        1560        1570
TCATCCATTCTATAGCGTCTTTACACCTTCTCCAGTCAATGCGCTTATTGGTAAAACCCTACTATCTCTAGCGCTTATATGTTCCGAATCTATTAAATACTTCTTTATATC
```

METHODS OF REGULATING PROTEIN GLYCOSYLATION

CROSS-REFERENCE TO RELATED APPLICATION

This application is a continuation-in-part of U.S. patent application Ser. No. 116,095, filed Oct. 29, 1987, now abandoned.

TECHNICAL FIELD

The present invention is directed generally toward methods of producing heterologous proteins or polypeptides, and more specifically, toward methods of regulating protein glycosylation.

BACKGROUND OF THE INVENTION

Recent advances in recombinant DNA technology have led to the use of fungal cells as hosts for the production of foreign polypeptides. Among the most widely utilized fungi is bakers' yeast (*Saccharomyces cerevisiae*). Yeast secretory peptides have been exploited to export heterologous proteins from yeast cells into the medium. The low number of natural yeast proteins exported into the medium facilitates the purification of exported heterologous proteins (Hitzeman et al., *Science* 219:620–625, 1983). The passage of proteins through the yeast secretory pathway provides for disulfide bond formation and glycoprotein glycosylation, modifications which in many cases are required to achieve proper folding and/or full biological activity.

The secretory pathway of yeast directs the transfer of oligosaccharide and mannose moieties, through two types of linkages, to glycosylation sites on secretion-directed proteins (Kukuruzinska et al., *Ann. Rev. Biochem.* 56:915–944, 1987). O-linked glycosylation is initiated with the transfer of one mannose moiety to Ser or Thr residues on the glycoprotein. The addition of core oligosaccharide structures to an Asn residue on a polypeptide chain constitutes an N-linked glycosidic linkage (Sheckman and Novick, in Strathern et al., eds., *Mol. Biol. of Yeast Saccharomyces: Metabolism and Gene Expression*, New York: Cold Spring Harbor Laboratory, pp. 361–393, 1982). The acceptor site for the addition of N-linked, core oligosaccharide structures is a tripeptide sequence of Asn-X-Ser or Asn-X-Thr, where X may be any amino acid, although not all of these tripeptide sequences are host to N-linked glycosylation. The tripeptide sequence acceptor sites found in yeast glycoproteins appear to be identical to those sites identified in mammalian glycoproteins (for review, see Kukurizinska et al., *Ann. Rev. Biochem.* 56:915–944, 1987). *Aspergillus nidulans* has also been shown to glycosylate foreign proteins at these tripeptide acceptor sequences.

Yeast has been shown to glycosylate foreign glycoproteins at N-linked acceptor sites shown to be glycosylated in nature, for example, tissue plasminogen activator (tPA), isolated from Bowes melanoma cells, has four potential N-linked gycosylation sites, of which three are glycosylated. tPA which has been expressed in yeast cells shows glycosylation at the same three sites. Calf prochymosin, which contains two potential N-linked glycosylation sites, of which only one is glycosylated, when expressed in yeast shows glycosylation at the same site as in calf cells. The N-linked, core oligosaccharide structure of yeast glycoproteins appears to be identical to similar oligosaccharide structures on mammalian glycoproteins (Ballou, in Strathern et al., eds., *Mol. Biol. of Yeast Saccharomyces: Metabolism and Gene Expression*, New York: Cold Spring Harbor Laboratory, pp. 335–360, 1982).

Outer chain glycosylation is often species-specific in structure, and this structure may play a role in the biological activity of proteins. For example, the outer chain oligosaccharides which are attached to the N-linked, core oligosaccharide structures on yeast-produced glycoproteins diverge in structure and content from outer chain oligosaccharides present on mammalian-produced glycoproteins. In yeast, outer chain oligosaccharides, consisting of a backbone of $\alpha 1 \rightarrow 6$ linked mannose residues to which mono-, di-, and trimannosyl branches are attached, are joined to N-linked oligosaccharide core structures. Yeast may glycosylate foreign proteins in this manner, resulting in the presence of outer oligosaccharide chains which can be markedly different from those of native material. This difference in outer chain oligosaccharide composition may result in reduction or loss of biological activity for those proteins whose conformation or activity is hindered by yeast glycosylation.

The presence of foreign oligosaccharide structures may pose a significant problem when considering the use of recombinant glycoproteins as therapeutic agents. For example, Ballou (*J. Biol. Chem.* 245:1197, 1970) and Suzuki et al. (*Jpn. J. Microbiol.* 12:19, 1968) have shown that the oligosaccharide chains of cell wall glycoproteins are the principal immunogens when whole yeast cells are injected into rabbits or goats. The oligosaccharide chains present on cell wall glycoproteins have been shown to be identical to the oligosaccharide chains present on secreted glycoproteins such as invertase (for review, see Sheckman and Novick, ibid.).

Foreign glycoproteins, including immunoglobulin chains, somatostatin, tissue plasminogen activator (tPA), the major envelope protein of Epstein-Barr virus (gp350) (Schultz et al., *Gene* 54:113–123, 1987), α-1-antitrypsin (AAT), and $\alpha^2\beta$haptoglobin (Van der Straten et al., *DNA* 5:126–136, 1986, have been expressed in yeast. Studies of yeast cells transformed with genes or cDNAs encoding these glycoproteins have shown that the protein products are heterogeneous with respect to the carbohydrate side chains. In most cases, the heterogeneous product consists of a mixture of hyperglycosyated forms of the protein. This heterogeneity and hyperglycosylation may render the products unsuitable for therapeutic use. Further, the heterogeneous nature of yeast-produced glycoproteins adds additional steps to their purification from the medium of secreting cells.

Several methods have been described which may be employed in an effort to reduce or remove carbohydrate residues from glycoproteins expressed in yeast. The methods include the use of glycosylation inhibitors, post-production deglycosylation and in vitro mutagenesis of cloned DNA sequences. Although these methods have been shown to be somewhat useful, they have met with only limited success.

The glycosylation inhibitor tunicamycin may be used to inhibit the addition of carbohydrate onto yeast-made proteins. The resultant proteins may not be active and may not be exported from the cell. In addition, tunicamycin treatment of yeast cells may not fully inhibit the N-linked glycosylation of proteins, must be used under very carefully controlled conditions, and cannot be used for extended incubations. The protein product from tunicamycin-treated cells would therefore contain a mixture of glycosylated and unglycosylated proteins and would require additional steps to remove the tunicamycin from the preparation.

In vitro enzymatic deglycosylation of polypeptides using endo-β-N-acetylglucosaminidase H (endo H) as described by Torrentino and Maley (*J. Biol. Chem.* 249:811-817, 1974) has been used to deglycosylate such yeast-produced proteins as somatostatin (Green et al., *J. Biol. Chem.* 261:7558-7565, 1986), α-1-antitrypsin (Van der Straten et al., ibid.), and α2βhaptoglobin (Van der Straten et al., ibid.). Endo H treatment, under nondenaturing conditions, of yeast-produced tpA fails to remove all of the carbohydrate and the resultant protein product remains heterogeneous in nature and thus unsuitable for therapeutic use. This method of in vitro deglycosylation has the drawback of adding an additional step to the processing of the protein product and necessitating the complete removal of the enzyme from commercial preparations of the protein. These extra steps increase the cost of commercial production and will not necessarily result in the removal of all the oligosaccharide side chains from the proteins.

Another approach to overcoming the problems associated with yeast-produced glycoproteins is the elimination of glycosylation sites through mutagenesis. Haigwood et al. (EP 227,462, 1987) and Meyhack et al. (EP 225,286, 1987) have described mutants of human tissue plasminogen activator in which one or all of the potential glycosylation sites are altered to prevent N-linked glycosylation. Meyhack et al. (ibid.) have reported that yeast-produced underglycosylated tPA retains biological activity. However, such proteins may not be stable and would therefore be unsuitable for commercial production. Furthermore, these mutations were generated by in vitro mutagenesis at each potential glycosylation site and the mutagenesis must be repeated on each gene or cDNA encoding a heterologous glycoprotein which is to be secreted from yeast. These mutations cause changes in the amino acid sequence, resulting in the production of mutant proteins which are not found in nature and which may have altered stability, half-life or solubility.

There is therefore a need in the art for improved methods of producing biologically active proteins from yeast with reduced glycosylation. The present invention provides such methods, which are widely applicable to yeast-secreted protein products. The methods also provide the advantage of fewer steps for the purification of the homogeneous protein product, which leads to a reduced cost for production of the protein of interest.

DISCLOSURE OF THE INVENTION

Briefly stated, the present invention discloses methods for producing a heterologous protein or polypeptide. Generally, one such method comprises (a) introducing into a fungal cell carrying a defect in a gene whose product is required for the addition of outer chain oligosaccharide moieties to glycoproteins a first DNA construct comprising a regulated promoter followed downstream by a DNA sequence which complements the defect; (b) introducing into the fungal cell a second DNA construct comprising a second promoter followed downstream by a DNA sequence encoding a secretion signal and a DNA sequence encoding a heterologous protein or polypeptide; (c) culturing the fungal cell under a first set of growth conditions such that the DNA sequence which complements the defect is expressed; (d) culturing the fungal cell under a second set of growth conditions such that the DNA sequence which complements the defect is not expressed and the DNA sequence encoding the heterologous protein or polypeptide is expressed; and (e) isolating the heterologous protein or polypeptide. Preferred fungal cells are Aspergillus and yeast.

A variety of proteins may be produced utilizing the method, including tissue plasminogen activator, urokinase, immunoglobulins, platelet-derived growth factor, plasminogen, thrombin, factor XIII, and analogs thereof.

Another aspect of the present invention discloses a fungal cell carrying a defect in a gene whose product is required for the addition of outer chain oligosaccharide moieties to glycoproteins, the cell transformed with a first DNA construct comprising a regulated promoter followed downstream by a DNA sequence which complements the defect, and a second DNA construct comprising a second promoter followed downstream by a DNA sequence encoding a secretion signal and a DNA sequence encoding a heterologous protein or polypeptide.

A related aspect of the present invention discloses a yeast cell having a Mnn9- phenotype and capable of producing colonies of normal morphologies in the absence of osmotic stabilization. Within preferred embodiments, the yeast cell carries a pep4 mutation or further carries a defect in the MNN1 gene.

Within a preferred aspect of the present invention, a method for producing a heterologous protein or polypeptide is disclosed, generally comprising (a) introducing into a yeast cell having a Mnn9- phenotype and capable of producing colonies of normal morphology in the absence of osmotic stabilization a DNA construct comprising a promoter, a DNA sequence encoding a secretion signal, and a DNA sequence encoding a heterologous protein or polypeptide; (b) culturing the cell under conditions such that the DNA sequence encoding the protein or polypeptide is expressed; and (c) isolating the heterologous protein or polypeptide. Within a particularly preferred embodiment, the cell is derived from the yeast strain ZY300. The promoter may be a constitutive promoter or a regulated promoter.

Within yet another aspect of the present invention, a method for identifying a yeast strain having a defect in a gene whose product is required for the addition of outer chain oligosaccharide moieties to glycoproteins is disclosed. The method generally comprises (a) culturing yeast cells having active proteinase B on solid medium to produce colonies; (b) permeabilizing the colonies; (c) overlaying the permeabilized colonies with a composition comprising azocoll, the composition having a pH greater than 4.0 and less than 7.4; (d) incubating the colonies under conditions sufficient to cause a clear halo to form around colonies exhibiting a Mnn9- phenotype; and (e) detecting the presence of a clear halo around the colonies and therefrom identifying yeast strains having a defect in a gene whose product is required for the addition of outer chain oligosaccharide moieties to glycoproteins.

Within another aspect of the present invention, a method of cloning a DNA sequence which complements a defect in a gene whose product is required for the addition of outer chain oligosaccharide moieties to glycoproteins is disclosed. The method generally comprises (a) transforming a yeast cell having a defect in the gene with a library of DNA fragments; (b) culturing the yeast cells on solid medium to produce colonies; (c) permeabilizing the colonies; (d) overlaying the permeabilized colonies with a composition comprising azocoll, the composition having a pH greater than 4.0 and less than 7.4; (e) incubating the colonies under conditions sufficient to cause a clear halo to form around colonies exhibiting Mnn9− phenotype; (f) selecting colonies which do not exhibit a clear halo; and (g) isolating from the selected colonies the DNA sequence which complements the defect.

These and other aspects of the present invention will become evident upon reference to the following detailed description and attached drawings.

BRIEF DESCRIPTION OF THE DRAWINGS

FIGS. 1A and 1B illustrate proposed structures for *Saccharomyces cerevisiae* modified core oligosaccharide produced in mnn9 and mnn1 mnn9 mutants. FIG. 1A illustrates the 13-mannose form of oligosaccharide produced by mnn9 mutants. FIG. 1B illustrates the 10-mannose form of oligosaccharide produced by mnn1 mnn9 mutants. A 9-mannose form of oligosaccharide has also been described. (M) is Mannose; (GlcNAc) is N-acetylglucosamine; (Asn) is an asparagine residue of the Asn-X-Ser or Asn-X-Thr acceptor sites; (6) indicates an $\alpha 1 \rightarrow 6$ linkage between mannoses; (3) indicates an $\alpha 1 \rightarrow 3$ linkage between mannoses; (2) indicates an $\alpha 1 \rightarrow 2$ 1 linkage between mannoses; and (4) indicates the an $\alpha 1 \rightarrow 4$ linkage between the mannose and the GcNAc.

FIGS. 4 and 4A illustrate the nucleotide sequence of the MNN9 gene and the derived amino acid sequence of the primary translation product. Numbers above the lines refer to the nucleotide sequence; negative numbers indicate the 5' noncoding sequence.

BEST MODE FOR CARRYING OUT THE INVENTION

Figure 2:
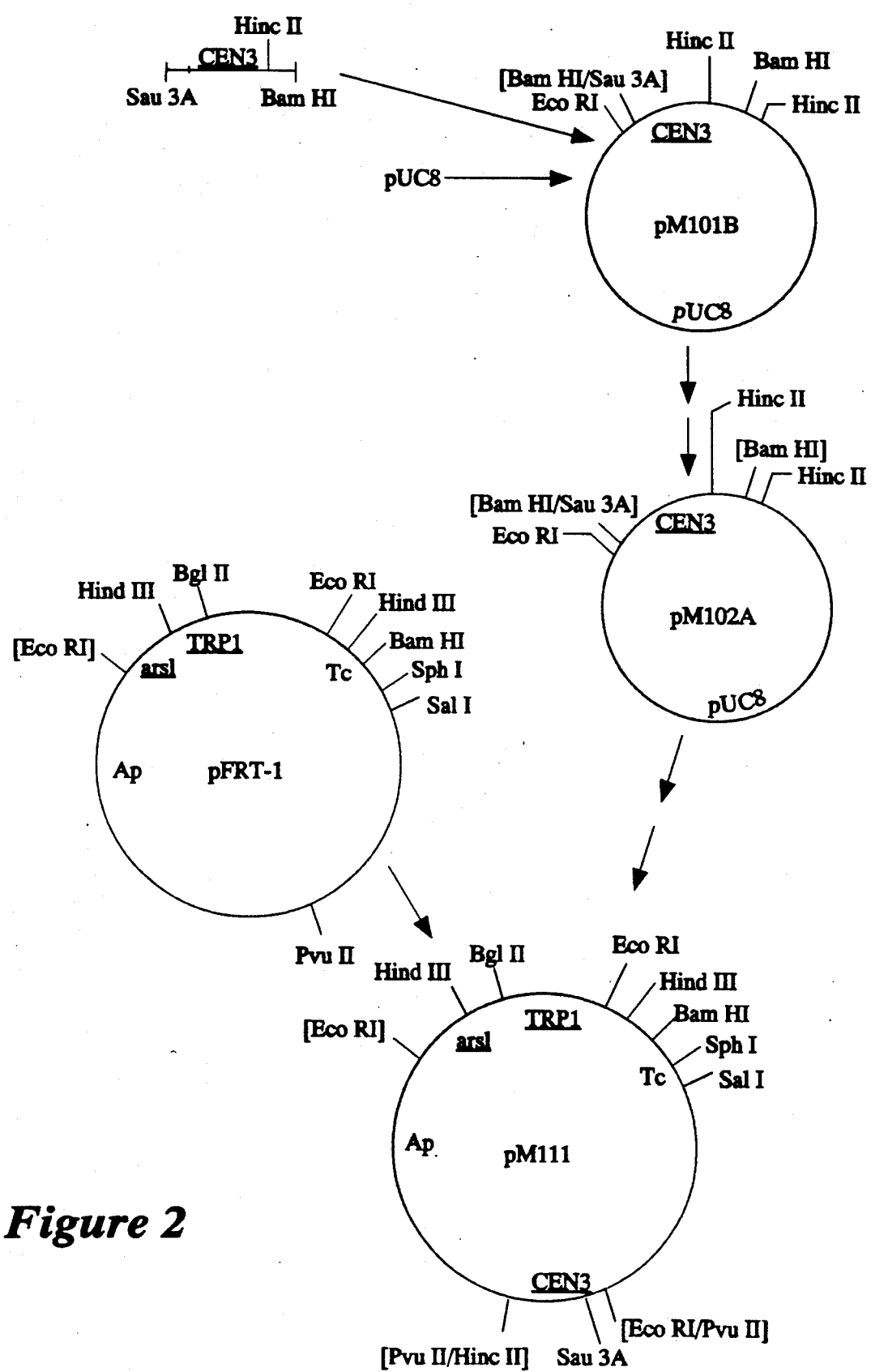
FIG. 2 illustrates the construction of pM111.

Prior to setting forth the invention, it may be helpful to an understanding thereof to set forth definitions of certain terms to be used hereinafter.

DNA construct: A DNA molecule, or a clone of such a molecule, either single- or double-stranded, which has been modified through human intervention to contain segments of DNA combined and juxtaposed in a manner which as a whole would not otherwise exist in nature.

Mating-type regulatory element: A DNA sequence to which yeast MAT gene products will bind, resulting in the repression of expression of genes linked to the sequence. The terms "operator" and "operator sequence" are also used to describe these elements.

Mnn9− phenotype: A yeast cell phenotype characterized by the production of exported or secreted glycoproteins which run on SDS-polyacrylamide gels as discrete, homogeneous species. These glycoproteins lack the hyperglycosylation characteristic of glycoproteins produced by wild-type yeast cells.

Modified core oligosaccharide: An N-linked carbohydrate side chain of a glycoprotein which contains two N-acetylglucosamine (GlcNAc) residues coupled to from 9 to 13 mannose residues. Representative modified core oligosaccharide structures are illustrated in FIGS. 1A and 1B.

Regulated promoter: A DNA sequence which directs transcription of a linked DNA sequence at levels which vary in response to external stimuli. Regulated promoters are, in general, either "on" (maximum transcription level) or "off" (little or no transcription), depending on a cell's environment, although in some cases intermediate levels may be obtained.

Secretion signal: A DNA sequence encoding a secretory peptide. A secretory peptide is an amino acid sequence characterized by a core of hydrophobic amino acids which acts to direct the secretion of a mature polypeptide or protein from a cell. Secretory peptides are typically found at the amino termini of newly synthesized proteins and are cleaved from the mature protein during secretion.

As noted above, the present invention describes methods by which heterologous glycoproteins may be secreted from fungal cells with modified core glycosylation. The methods described herein are particularly advantageous in that they allow the production of glycoproteins containing modified core oligosaccharide moieties through the use of a host cell having a defect in a gene whose product is required for the addition of outer chain oligosaccharide moieties to glycoproteins. These methods do not rely on the more expensive methods of post-production modification of the glycoproteins nor do the methods rely on the addition of glycosylation-inhibiting factors to the cells or cell products.

Fungal cells, including species of yeast (e.g., Saccharomyces spp., *Schizosaccharomyces pombe*), or filamentous fungi (e.g., Aspergillus spp., Neurospora spp.) may be used as host cells for the present invention. The yeast *Saccaromyces cerevisiae*, for example, carries genes (MNN7–MNN10) which enable yeast cells to add outer chain oligosaccharide moieties to the oligosaccharide core structure of secretion-directed proteins. Mutants with defects in these genes (mnn7–mnn10) do not add outer mannose moieties to glycoproteins, resulting in glycoproteins with a homogeneous amount of glycosylation.

A gene required for the addition of outer chain oligosaccharide moieties may be identified in a number of ways. One method, for example, has been described by Ballou et al. (*J. Biol. Chem.* 255:5986–5991, 1980). In this method, antibodies are raised against the mannose moieties present on the surface of yeast cells, preferably against those mannose moieties present on the surface of yeast mnn2 mutant cells. Yeast cells, preferably haploid mnn2 cells, are mutagenized. The antibodies, preferably labeled antibodies, are then used to identify populations amongst the mutagenized cells which fail to bind antibody. These mutants are then crossed with each other to establish genetic complementation groups. Complementation between two mutations results in a diploid with the pre-mutagenized parent phenotype. A preferred method for screening for the pre-mutagenized parent phenotype is to use antibodies directed against the mannose moieties of the parent strain. By this method, four complementation groups (designated mnn7–mnn10) are established. Glycosylation mutants of other fungi may be isolated using this method of mutant identification.

An alternative method is to use the properties of concanavalin A, a lectin which has a high specificity for oligosaccharides containing three or more mannose residues. Mutagenized cells are passed over a concanavalin A column. Cells which exhibit cell surface glycoproteins with less than three mannose residues will elute off such a column and may be isolated from the effluent. Similarly, a third method consists of identifying glycosylation mutants using labeled concanavalin A which will bind to cells which exhibit cell surface glycoproteins with more than three mannose residues and not to glycosylation mutants exhibiting glycoproteins with three or fewer mannose moieties.

A fourth method of isolating glycosylation mutants is to introduce a DNA construct comprising a sequence encoding a secretion signal followed by a heterologous gene or cDNA encoding a glycoprotein, preferably a glycoprotein known to be highly glycosylated, into a host strain. The transformed host strain is mutagenized and the mutagenized population is screened for the production of heterologous protein with reduced glycosylation.

A preferred method of screening for mnn9 mutants involves the unexpected response of mnn9 cells when assayed for proteinase B. Briefly, cells which are prB+ (cells which have active proteinase B) are grown on a solid complex-rich (chemically undefined) medium, comprising a nitrogen source, inorganic salts, vitamins, a carbon source, and an osmotic stabilizer, or under selective conditions, on solid synthetic medium supplemented with an osmotic stabilizer. Solid media include those which contain agar, agarose, gelatin or similar agents. A particularly preferred complex-rich medium is YEPDS (2% yeast extract, 1% peptone, 2% glucose, 1 M sorbitol). Colonies grown on complex-rich media are permeabilized by spheroplasting or exposure to fumes of a solvent which affects membranes without causing widespread lysis. Suitable solvents include toluene, chloroform or other similar solvents generally known in the art. Colonies grown on synthetic medium are either grown on or transferred to filters (to compensate for the low pH of synthetic medium), such as nitrocellulose filters or paper filters, and lysed by exposure of the filters to zymolyase or preferably by immersion in liquid nitrogen. Colonies grown on or transferred to paper filters may be permeabilized by exposure to solvent fumes. The filters are then laid on solid rich medium. The permeabilized colonies are then overlayed with top agar, comprising azocoll, preferably approximately 10 mg/ml of top agar and having pH greater than 4.0 and less than 7.4, preferably about 7.0. The plates are incubated at a temperature between 20° C. and 40° C., preferably at 37° C., for between 3 hours and 24 hours, preferably within the range of 5 to 8 hours. Colonies which exhibit a Mnn9− phenotype form a clear halo around the colonies.

The mnn7–mnn9 mutants are then used to clone the corresponding genes. By way of example, the MNN9 gene was cloned from a pool of yeast DNA fragments, more specifically, a pool of genomic yeast DNA fragments. Within the present invention, a library of DNA fragments cloned into a yeast/E. coli vector is made, for example, by the method described by Nasmyth and Reed (Proc. Natl. Acad. Sci. USA 77:2119-2123, 1980). Briefly, genomic yeast DNA is made and partially digested with a suitable restriction enzyme to generate fragments that are between about 5 kb and about 20 kb. Preferred enzymes are four-base cutters such as Sau 3A. The generated fragments are then ligated into a suitable yeast/E. coli shuttle vector which has been linearized by digestion with the appropriate restriction enzyme. It is preferable to dephosphorylate the linearized vector to prevent recircularization. Suitable vectors include YEp13 (Broach et al., Gene 8:121-133, 1979), YRp7 (Stinchcomb et al., Nature 275:39-45, 1979), pJDB219 and pJDB248 (Beggs, Nature 275:104-108, 1978), YCp50 (Kuo and Campbell, Mol. Cell. Biol. 3:1730-1737, 1983) and derivatives thereof. Such vectors will generally include a selectable marker. Selectable markers may include any dominant marker for which a method of selection exists. Such selectable markers may include a nutritional marker, for example, LEU2, which allows selection in a host strain carrying a leu2 mutation, or a gene which encodes antibiotic resistance, for example, chloramphenicol transacetylase (CAT), which enables cells to grow in the presence of chloramphenicol. Alternatively, they may include an "essential gene" as a selectable marker (Kawasaki and Bell, EP 171,142), for example, the POT1 gene of Schizosaccharomyces pombe, which complements a tpi1 mutation in the host cell, allowing cells to grow in the presence of glucose. It is preferable to transform the ligation mixture into an E. coli strain, for example, RR1 (Bolivar et al., Gene 2:95-113, 1977), to amplify the library of yeast DNA fragments. To facilitate selection of transformants in yeast, plasmid DNA is made from the E. coli transformant library and is introduced into yeast cells which are genotypically mnn9 and may contain a genetic defect which is complemented by a suitable marker present on the yeast/E. coli shuttle vector. Transformant colonies are selected by an appropriate selection method for the presence of the plasmid in the host cell. The transformants are then screened for the complementation of the mnn9 deficiency. Screening methods may include using antibodies directed against the mannose moieties of wild-type yeast cells, and determining the carbohydrate content of the mutants. A preferred method of screening for the complementation of the mnn9 mutation utilizes the proteinase B assay described above. Colonies containing a cloned MNN9 gene are identified by the absence of a clear halo.

MNN9 gene clones may be confirmed to be plasmid borne, as opposed to revertants, by testing for the loss of plasmid. Plasmid loss is achieved by growing the yeast cells under nonselective conditions to determine if the Mnn+ phenotype is lost with the loss of the plasmid. DNA from the positive clones is made using methods known in the art (for example, Hartig et al., Mol. Cell. Biol. 6:1206-1224, 1986). Restriction mapping may be carried out to determine the smallest fragment of the genomic insert needed to complement the mnn9 deficiency. The DNA sequence may also be determined for the cloned gene.

The genes or cDNAs encoding MNN7, MNN8 and MNN10 may be cloned using a library of yeast DNA fragments as described above to complement a genetic deficiency in MNN7, MNN8, or MNN10, respectively, in a host strain. However, the preferred screening method used for identifying MNN9 gene clones may not be as well suited for identifying MNN7, MNN8, or MNN10 gene clones. In this case, preferred screening methods include using antibodies directed against wild-type oligosaccharide moieties and the determination of oligosaccharide content (as described in Ballou, ibid., 1970, and Ballou, ibid., 1980). Positive clones may be further characterized as described for the MNN9 gene clone.

According to the present invention, the addition of outer chain glycosylation may be controlled through the use of a regulated promoter to drive the expression of a cloned MNN7, MNN8, MNN9 or MNN10 gene. Cells which exhibit the mnn7-mnn10 phenotype are slow to grow and are exceptionally sensitive to cell lysis in the absence of osmotic support. The regulated expression of these genes during active cell growth will allow the cells to grow in a wild-type manner with wild-type glycosylation of glycoproteins and cell wall components. The regulated promoter is then turned off to permit production of a heterologous protein or polypeptide with only core glycosylation. The expression unit, comprising a regulated promoter fused to the cloned MNN gene, may be plasmid borne, in which case the expression unit will complement a corresponding mnn mutation in the host strain. Alternatively, the expression unit may be integrated into the host genome.

The use of regulated promoters to drive the expression of both heterologous and homologous DNA sequences in yeast is well known in the art. The regulation of such sequences is realized through the use of any one of a number of regulated promoters. Preferred regulated promoters for use in the present invention include the ADH2 promoter (Young et al., in *Genetic Engineering of Microorganisms for Chemicas*, Hollaender et al., eds., New York:Plenum, p. 335, 1982), and the ADH2-4C promoter (Russell et al., *Nature* 304:652–654, 1983).

A particularly preferred promoter is the MFα1 promoter (Kurjan and Herskowitz, *Cell* 30:933–943, 1982). Other particularly preferred promoters are the SXR promoters (described in co-pending, commonly assigned U.S. patent application Ser. No. 889,100, which is incorporated by reference herein in its entirety), which combine one or more mating-type regulatory elements and a constitutive promoter (e.g., the TpI1 promoter).

Mating-type regulatory elements may be isolated from the upstream regions of yeast genes which are expressed in a mating-type specific manner or may be constructed de novo and are generally from about 20 base pairs to about 32 base pairs in length. Promoters of this type are used in a yeast strain that contains a conditional mutation in a gene required for the expression of the silent mating-type loci. The term "conditional mutation" is understood to mean a mutation in a gene which results in the reduction or lack of the active gene product under one set of environmental conditions and a normal (wild-type) level of the active gene product under a different set of environmental conditions. The most common conditional mutations are temperature-sensitive mutations. Temperature-sensitive mutations in genes required for the expression of the silent mating-type loci including the sir1, sir2, sir3 and sir4 mutations. The temperature-sensitive mutation sir3-8 is particularly preferred.

The sir3-8 mutation (also known as ste8, Hartwell, *J. Cell Biol.* 85:811, 1980) is a temperature-sensitive mutation which blocks the expression of information at the HML and HMR lloci at 25° C. while at 35° C. the expression of these loci is not blocked and the information at the HML and HMR loci is expressed. The mating-type regulatory elements used in the SXR promoters are derived from the STE2 gene. These elements, placed within a promoter, will regulate the expression of the gene of interest dependent upon the presence or absence of an active SIR3 gene product.

Yeast host strains for use in the present invention will contain a genetic defect within the MNN7, MNN8, MNN9 or MNN10 genes, resulting in the inability of the cell to add outer chain oligosaccharide moieties. This defect may be, for example, a mnn9 mutation as described by Ballou et al. (ibid., 1980) or, preferably, a gene disruption, such as a disruption of the MNN9 gene. A gene disruption may be a naturally occurring event or an in vitro manipulation in which the coding sequence of a gene is interrupted, resulting in either the production of an inactive gene product or no gene product. The interruption may take the form of an insertion of a DNA sequence into the coding sequence and/or the deletion of some or all of the coding sequence resulting in no protein product or premature translation termination. A gene disruption, comprising insertion of a DNA sequence and deletion of native MNN coding sequence, will not revert to wild-type as has been found with the mnn point mutations.

Gene disruptions may be generated essentially as described by Rothstein (in *Methods in Enzymology*, Wu et al., eds., 101:202–211, 1983). A plasmid is constructed which comprises DNA sequences which are homologous to the region in the genome containing, for example, the MNN9 gene, preferably including the coding sequence and both 5' and 3' flanking sequences of the cloned MNN9 gene. The sequence encoding the MNN9 gene is disrupted, preferably by the introduction of a selectable marker. This selectable marker may interrupt the coding sequence of the gene, or it may replace some or al of the coding sequence of the gene. The selectable marker may be one of any number of genes which exhibit a dominant phenotype for which a phenotypic assay exists, to enable deletion mutants to be selected. Preferred selectable markers are those which may complement host cell auxotrophy, provide antibiotic resistance or enable a cell to utilize specific carbon sources, including URA3 (Botstein et al., *Gene* 8:17, 1979), LEU2 (Broach et al., ibid.) and HIS3 (Struhl et al., ibid.). The URA3 marker is particularly preferred. Other suitable selectable markers include the CAT gene, which confers chloramphenicol resistance on yeast cells, or the lacZ gene, which results in blue colonies due to the expression of active β-galactosidase. Linear DNA fragments comprising the disrupted MNN gene, preferably isolated from the vector fragments, are introduced into the host cell using methods well known in the literature (e.g., Beggs, ibid.). The yeast host cell may be any one of a number of host cells generally available, for example, from the American Type Culture Collection, Rockville, Md. or the Yeast Genetic Stock Center, Berkeley, Calif. The host cell may carry a genetic defect which is complemented by the selectable marker used to disrupt the MNN coding sequence. Suitable yeast strains include SEY2101 (MATa ade2-101 leu2-3,112 ura3-52 suc2-Δ9 gal2) or ZY100 (MATa ade2-101 leu2-3,112 ura3-52 suc2-Δ9gal2 Δpep4::CAT). Integration of the linear fragments comprising selectable markers is detected by selection or screening using the dominant marker and proven by, for example, Southern analysis (Southern, *J. Mol. Biol.* 98:503–517, 1975) and phenotype testing.

It is preferable that the host cell contain a deficiency in the MNN1 gene as well as a deficiency in the MNN7, MNN8, MNN9, or MNN10 gene. A deficiency in the MNN1 gene eliminates the terminal α1→3-linked mannose in all of the N-linked glycoproteins of the cell (for review, see Ballou, ibid., 1982). This mutation in combination with, for example, a mnn9 mutation, will allow the host cells to produce glycoproteins containing modified core oligosaccharide structures with 9 or 10 mannose moieties. A mnn1 mutation may be introduced into a mnn9 strain, preferably a strain carrying a mnn9 gene disruption, by crossing it into the desired strain or preferably by disrupting the MNN1 gene in a strain carrying a mnn9 disruption. To disrupt the MNN1 gene, it must first be cloned. The MNN1 gene may be cloned as described previously, using a library of yeast DNA fragments in a suitable yeast shuttle vector. It is preferable to amplify the library by first transforming it into an *E. coli* host, preferably strain RR1. DNA is made from the transformed *E. coli*, and it is transformed into a yeast host which is mnn1 and may contain a genetic deficiency which is complemented by a selectable marker present on the yeast/*E. coli* shuttle vector. To facilitate identification of MNN1 gene clones, transformants are first selected for the presence of the plasmid in the host cell. The transformants are then screened for the complementation of the mnn1 deficiency. Screening methods for the complementation of mnn1 include using antibodies directed against either wild-type oligosaccharide moieties or oligosaccharide moieties present on mnn1 cells to identify transformants carrying DNA sequences which confer a Mnn1+ phenotype on the host cell (described by Ballou, ibid., 1970 and Ballou, ibid., 1982). A preferred method for screening transformants for MNN1 complementation is to use antibodies directed against the terminal $\alpha 1 \rightarrow 3$-linked mannose units of wild-type cells to identify positive clones. MNN1 gene clones may be confirmed to be plasmid borne by testing for the loss of plasmid coupled with loss of the Mnn1+ phenotype as described previously. Restriction mapping may be carried out to determine the smallest fragment of the genomic insert needed to complement the mnn1 deficiency. The DNA sequence may also be determined for the cloned gene.

In a preferred embodiment, a yeast host cell which contains a genetic deficiency in MNN7, MNN8, MNN9 or MNN10 also contains a conditional mutation in a gene which is required for the expression of the silent mating-type loci. Mutations in these genes permit the use of promoters containing mating-type regulatory elements as described above. A particularly preferred conditional mutant is sir3-8. Yeast strains having defects such as sir3-8 are widely available, such as from the Yeast Genetic Stock Center, Berkeley, Calif., or may be prepared using standard techniques of mutation and selection. The sir3-8 mutation may be introduced into a strain containing a genetic deficiency in MNN7, MNN8, MNN9, OR MNN10 by crossing or by using standard techniques of mutation and selection. To optimize production of heterologous proteins, it is preferred that the host strain carries a mutation, such as the pep4 mutation (Jones, *Genetics* 85:23-33, 1977), which results in reduced proteolytic activity.

As noted above, the regulated MNN7, MNN8, MNN9 or MNN10 expression unit, whether plasmid borne or integrated, is used in conjunction with a second DNA construct comprising a second promoter and a sequence encoding a secretion signal fused to a heterologous gene or cDNA of interest. A preferred embodiment of the invention is the use of a regulated promoter different from that directing expression of the cloned MNN gene as the second promoter, the use of which provides the ability to vary the expression of the heterologous gene or cDNA to prevent the production of a protein product containing outer chain oligosaccharide moieties. Preferred secretion signals include those derived from the yeast MFα1 (Kurjan et al., U.S. Pat. No. 4,546,082; Singh, EP 123,544), PHO5 (Beck et al., WO 86/00637), SUC2 (Carlson et al., *Mol. Cell. Biol.* 3:439-447, 1983) and BAR1 (MacKay et al., U.S. Pat. No. 4,613,572; MacKay, WO 87/02670) genes.

The expression unit comprising the heterologous gene or cDNA of interest may be carried on the same plasmid as a plasmid-borne regulated MNN expression unit and subsequently transformed into a host cell. Alternatively, the expression unit comprising the heterologous gene or cDNA may be on a separate plasmid, or integrated into the host genome. Integration is a recombination event which occurs at a homologous site and results in the insertion of a DNA sequence at that site. These expression units may be used in any combination with a plasmid-borne or integrated, regulated MNN gene: These combinations allow normal expression of the MNN gene with unimpaired cell growth during the exponential phase of cell growth, with normal glycoprotein synthesis. In a preferred embodiment, during active cell growth the growth conditions of the culture are regulated to prevent the heterologous gene from being expressed. When the cells reach optimal density, the growth conditions are selectively altered, thereby blocking the expression of the MNN gene, and allowing the heterologous protein product with modified core glycosylation to be synthesized. Heterologous proteins and polypeptides which may be produced according the present invention include growth factors (e.g., platelet-derived growth factor), tissue plasminogen activator, urokinase, immunoglobulins, plasminogen, thrombin, factor XIII and analogs thereof.

According to the present invention, another method for controlling the addition of outer chain oligosaccharides to secretion-directed glycoproteins involves the isolation of a unique and unexpected mnn9 disruption mutant. This mutant provides a yeast host which is able to produce heterologous glycoproteins containing modified core glycosylation, without the need to manipulate culture conditions. A mnn9 disruption was made as previously described. Briefly, a DNA construct, comprising the MNN9 coding sequence which has been disrupted with a selectable marker (URA3 gene), was introduced into strain SEY2101. Transformants were selected for their ability to grow on synthetic medium lacking uracil. Transformants were assayed for the presence of the Mnn9- phenotype. Southern analysis was done to confirm the disruption of the MNN9 gene. A positive clone was identified which retained the URA3 marker and the Mnn9- phenotype and exhibited a pattern on Southern analysis (Southern, *J. Mol. Bio.* 98 503-517, 1975) showing that the MNN9 gene is intact. Pulsed-field gel electrophoresis (Southern et al., *Nuc. Acids Res.* 15:5925-5943, 1987) on genomic DNA derived from this strain has shown that the mnn9 disruption isolate has undergone chromosome aberrations involving at least chromosomes V and VIII. The strain, designated ZY300 (ATCC Accession No. 20870), grows faster than the mnn9 point mutation isolated by Ballou (ibid., 1980) or other confirmed mnn9 deletion strains. Analysis of the strain shows that it is apparently able to grow without osmotic support. Transformation of this strain with certain yeast plasmids (e.g., YEp13), which contain REP3 and the replication origin, but not REp or REP2, has shown that the plasmids are unstable due to the variant 2 micron plasmid present in the parent strain. Yeast vectors which contain REP1, REP2. REP3 and a replication origin or which utilize a centromere fragment and a replication origin are stable in the strain. It is preferable to cure the strain of the variant 2 micron plasmid and replace it with a wild-type 2 micron plasmid to allow the strain to utilize yeast vectors of the YEp13 type. For production of foreign proteins, a DNA construct comprising a promoter and a sequence encoding a secretion signal followed by a sequence encoding a polypeptide or protein of interest is introduced into strain ZY300. The promoter may be a regulated or constitutive promoter. The resultant proteins are homogeneous in nature and lack the characteristic yeast hyperglycosylation. It is preferable to introduce both a pep4 disruption and a mnn1 disruption in ZY300. Disruptions of these cloned genes are carried out in a manner similar to the gene disruption described previously.

Techniques for transforming fungi are well known in the literature and have been described, for instance, by Beggs (ibid.), Hinnen et al. (*Proc. Natl. Acad. Sci. USA* 75:1929-1933, 1978), Russell (*Nature* 301:167-169, 1983) and Yelton et al. (*Proc. Natl. Acad. Sci. USA* 81:1740-1747, 1984). Host strains may contain genetic defects in genes which are complemented by the selectable marker present on the vector. Such genetic defects include nutritional auxotrophies, for example, leu2, which may be complemented by the LEU2 gene and defects in genes required for carbon source utilization, for example, tpi1, which may be complemented by the POT1 gene of *Schizosaccharomyces pombe*. Choice of a particular host and selectable marker is well within the level of ordinary skill in the art.

Proteins produced according to the present invention may be purified by conventional methods. Particular purification protocols will be determined by the nature of the specific protein to be purified. Such determination is within the ordinary level of skill in the art. Generally, the cell culture medium will be separated from the cells and the protein will be isolated from the medium. Useful isolation techniques include precipitation, immunoadsorption and fractionation or a variety of chromatographic methods.

EXAMPLES

Example 1

Cloning of the *S. cerevisiae* MNN9 Gene

TABLE 1

| YEAST GENOTYPES | |
|---|---|
| LB347-1C | MATα mnn9 gal2 |
| ZA447 | MATa lea2-3,112 barl-1 gal2 ura3 |
| XV732-1-9A | MATα leu2-3,112 ura3 mnn9 gal2 |
| XP660-2A | MATa leu2-3,112 barl-1 trp1 gal2 |
| XCY1-5D | MATa leu2-3,112 ura3 trp1 mnn9 |
| SEY2101 | MATa leu2-3,112 ade2-101 ura3-52 suc2-Δ9 gal2 Δpep4::CAT |
| ZY100 | MATa leu2-3,112 ade2-101 ura3-52 suc2-Δ9 gal2 Δpep4::CAT |
| ZY300 | MATa leu2-3,112 ade2-101 ura3-52 suc2-Δ9 gal2 mnn9::URA3::tl-1 |
| ZY400 | MATa leu2-3,112 ade2-101 ura3-52 suc2-Δ9 gal2 Δpep4::CAT mnn9::URA3 |
| 381G-59a | MATa sir3-8 SUP4-3 ade2-1 his4-580 lys2 trp1-1 tyr1 cry1 |
| A2 | MATα leu2-3,112 his3-11,15 can1 |
| XL1-4B | MATa leu2-3,112 trp1-1 ade2-1 lys2 sir3-8 |
| XCY15-3C | MATα ade2-1 leu2-3,112 Δmnn9::URA3 |
| XCY42-28B | MATa sir3-8 Δmnn9::URA3 leu2-3,112 trp1-1 ade2-1 lys2 Δpep4::CAT |
| LB1-22D | MATα mnn1 gal2 SUC2 mal CUP1 |

A. Construction of Strain XCY1-5D

A *S. cerevisiae* strain having the mnn9 mutation and genetic defects in the URA3, LEU2, and TRP1 genes was constructed using parent strains listed in the table. Genetic methods and media used are generally known in the art. (See, for example: R. K. Mortimer and D. C. Hawthorne, in *Yeast Genetics*, A. H. Rose and J. S. Harrison, eds., London:Academic Press, Inc., ltd., p. 385-460; and Hartig et al., ibid.) Strain LB347-1C (Tsai et al., *J. Biol. Chem.* 259:3805-3811, 1984) was crossed with ZA447. Zygotes were pulled from the mating mixture to isolate diploids. A diploid colony designated XV732 was sporulated and dissected. Tetrad analysis of the spores showed a 2:2 segregation for small colonies when the spores were grown on medium without osmotic stabilization. (Small colony size on non-osmotically stabilized medium correlated with the presence of the mnn9 gene.) A spore which developed into a very small colony with leucine and uracil auxotrophies was chosen and designated XV732-1-9A. This spore was crossed with XP660-2A. Diploids were selected on minimal medium (Table 2) supplemented with 80 mg/l leucine to yield the diploid XCY1. XCY1 was sporulated and dissected. Tetrad analysis was carried out on the spores. Spore XCY1-5D (MATα mnn9 leu2-3 leu2-112 trp1 ura3 gal1) was selected as the host strain for cloning the MNN9 gene.

TABLE 2

| MinD | |
|---|---|
| 20 g | glucose |
| 6.7 g | Yeast Nitrogen Base without amino acids (Difco Laboratories, Detroit, Mich.) |
| 18 g | Agar |

Mix all the ingredients in distilled water. Add distilled water to a final volume of 1 liter. Autoclave 15 minutes. Pour plates and allow to solidify.

-LeuDS plates 20 g glucose
6.7 g Yeast Nitrogen Base without amino acids (Difco Laboratories, Detroit, Mich.)
40 mg adenine
30 mg L-arginine
50 mg L-aspartic acid
20 mg L-histidine free base
60 mg L-isoleucine
40 mg L-lysine-mono hydrochloride
20 mg L-methionine
60 mg L-phenylalanine
50 mg L-serine
50 mg L-tyrosine
40 mg uracil
60 mg L-valine
60.75 g sorbitol
18 g Agar Mix all the ingredients in distilled water. Add distilled water to a final volume of 1 liter. Autoclave 15 minutes. After autoclaving add 150 mg L-threonine and 40 mg L-tryptophan. Pour plates and allow to solidify.

-LeuDS

Use the recipe for -LeuDS pates, but omit the agar.

-LeuD plates

Use the recipe for -LeuDS plates, but omit the sorbitol.

-LeuD

Use the recipe for -LeuDS plates, but omit the sorbitol and agar.

-TrpDS plates 20 g glucose
6.7 g Yeast Nitrogen Base without amino acids (Difco Laboratories, Detroit, Mich.)
40 mg adenine
30 mg L-arginine
50 mg L-aspartic acid
20 mg L-histidine free base
60 mg L-isoleucine
80 mg L-leucine
40 mg L-lysine-mono hydrochloride
20 mg L-methionine
60 mg L-phenylalanine
50 mg L-serine
50 mg L-tyrosine
40 mg uracil
60 mg L-valine
60.75 g sorbitol
18 g Agar Mix all the ingredients in distilled water. Add distilled water to a final volume of 1 liter. Autoclave 15 minutes. After autoclaving add 150 mg L-threonine. Pour plates and allow to solidify.

-TrpD

Use the recipe for -TrpDS, but omit the sorbitol and agar.

YEPDS plates 20 g glucose
10 g Bacto-peptone (Difco)
20 g yeast extract (Difco)
60.75 g sorbitol
18 g Agar Mix all ingredients in distilled water. Add distilled water to a total volume of 1 liter. Autoclave 25 minutes. Pour plates and allow to solidify.

YEPDS

Use the recipe for YEPDS plates, but omit the agar.

YEPD plates 20 g glucose
10 g Bacto-peptone
20 g yeast extract
18 g agar

Mix all ingredients in distilled water. Add distilled water to a total volume of 1 liter. Autoclave 25 minutes. Pour plates and allow to solidify.

YEPD

Use the recipe for YEPD plates but omit the agar.

-UraDS plates 20 g glucose
6.7 g Yeast Nitrogen Base without amino acids (Difco Laboratories, Detroit, Mich.)
40 mg adenine
30 mg L-arginine
50 mg L-aspartic acid
20 mg L-histidine free base
60 mg L-isoleucine
80 mg L-leucine
40 mg L-lysine-mono hydrochloride
20 mg L-methionine
60 mg L-phenylalanine
50 mg L-serine
50 mg L-tyrosine
60 mg L-valine
60.75 g sorbitol
18 g Agar Mix all the ingredients in distilled water. Add distilled water to a final volume of 1 liter. Autoclave 15 minutes. After autoclaving add 150 mg L-threonine and 40 mg L-tryptophan. Pour plates and allow to solidify.

-Leu-TrpDS 20 g glucose
6.7 g Yeast Nitrogen Base without amino acids (Difco Laboratories, Detroit, Mich.)
40 mg adenine
30 mg L-arginine
50 mg L-aspartic acid
20 mg L-histidine free base
60 mg L-isoleucine
40 mg L-lysine-mono hydrochloride
20 mg L-methionine
60 mg L-phenylalanine
50 mg L-serine
50 mg L-tyrosine
40 mg uracil
60 mg L-valine 60.75 g sorbitol
18 g Agar Mix all the ingredients in distilled water. Add distilled water to a final volume of 1 liter. Autoclave 15 minutes. After autoclaving add 150 mg L-threonine. Pour plates and allow to solidify.

M9+CA+amp+W 6 g $Na_2HPO_4 \cdot H_2O$
3 g $KH_2PO_4$
0.5 g NaCl
1 g $NH_4Cl$
5 g casamino acids
1 ml 1 M $MgSO_4$
0.2 ml 0.5 M $CaCl_2$
5 ml 40% glucose
10 ml 1 mg/ml thiamine B1
2 ml 10 mg/ml L-tryptophan Dissolve ingredients in distilled water. Add distilled water to a final volume of one liter. Autoclave 25 minutes. After autoclaving, add 100 mg ampicillin.

M9+CA+amp

Use the recipe for M9+CA+amp+W, but omit the tryptophan.

B. Construction of the plasmid pM111

As illustrated in FIG. 2, a yeast shuttle vector was constructed which contained YRp7 (Stinchcomb et al., ibid.) vector sequences and the yeast centromere CEN3. A 630 bp Bam HI-Sau 3A fragment, comprising the yeast CEN3 sequences derived from pYe(CEN3)41 (Clarke and Carbon, *Nature* 287:504–509, 1980), was ligated into pUC8 which had been linearized by digestion with Bam HI and dephosphorylated with bacterial alkaline phosphatase. The ligation mixture was transformed in *E. coli* strain JM83. Plasmid DNA was made from the resultant transformants and cut with Bam HI to determine the presence of the CEN3 fragment. Positive clones were digested with Eco RI and Bam HI to determine the orientation of the insert. A clone with the CEN3 fragment in the proper orientation was designated pM101B. plasmid pM101B was linearized by digestion with Bam HI and treated with DNA polymerase I Klenow fragment to blunt the cohesive ends. The linearized plasmid was recircularized. The resultant plasmid, pM102A, was linearized by digestion with Hinc II and then cut with Eco RI to isolate the 0.6 kb CEN3 fragment. The Hinc II-Eco RI fragment was treated with DNA polymerase I Klenow fragment to fill in the Eco RI cohesive end, resulting in a 0.6 kb CEN3 fragment with blunt ends. Plasmid pFRT-1, comprising YRp7 which has had the Eco RI site distal to the 5' end of the TRP1 gene destroyed, was linearized by digestion with Pvu II. The pFRT-1 linear fragment was ligated with the 0.6 kb CEN3 fragment and the ligation mixture was transformed into *E. coli* strain RR1. DNA made from the resulting transformants was digested with Eco RI to confirm the presence of the insert and to determine the orientation of the CEN3 insert. (In one orientation, the Eco RI site is regenerated by ligation to the Pvu II blunt end.) The resultant plasmid was designated pM111.

C. Cloning the MNN9 gene

A pool of yeast genomic fragments from strain X2180 (ATCC 26109) cloned into the vector pM111 was used as the starting material for isolating the MNN9 gene. Briefly, genomic DNA was partially cut with Sau 3A and the resulting genomic fragments were cloned into the Bam HI site of the vector pM111. The average size of the inserts was 8 kb.

The pool of genomic DNA in pM111 was transformed into strain XCY1-5D essentially as described by Beggs (*Nature* 275:104-108, 1978). Transformants were selected for their ability to grow on -TrpDS plates (Table 2).

The transformant colonies were resuspended and replated using the method described by MacKay (*Methods In Enzymology* 101:325-343, 1983). The transformant colonies, suspended in top agar, were mixed and resuspended in -TrpD (Table 2)+0.5 M KCl to free the cells from the top agar. This mixture was grown for 2 hours at 30° C. and plated on -TrpDS plates. Colonies were allowed to grow on the -TrpDS plates at 30° C. Colonies were then picked to master -TrpDS plates in a grid formation. Replicas of the master plates were made onto -TrpDS plates and allowed to grow before MNN9 phenotype was determined.

Approximately 3,000 positive colonies were assayed for the presence of the MNN9 phenotype using the method described in Section D below. Sixteen colonies were found to consistently complement the mnn9 mutation present in the host strain and their ability to do so was linked to the presence of the plasmid. Plasmid DNA was isolated from the sixteen positive colonies as described by Hartig et al (*Mol Cell. Biol.* 6:2106-2114, 1986) and transformed into *E. coli* strain RR1. Plasmid DNA was isolated from the *E. coli* transformants and was subjected to restriction enzyme analysis. Fifteen of the plasmids showed two common Xba I sites.

Figure 3:
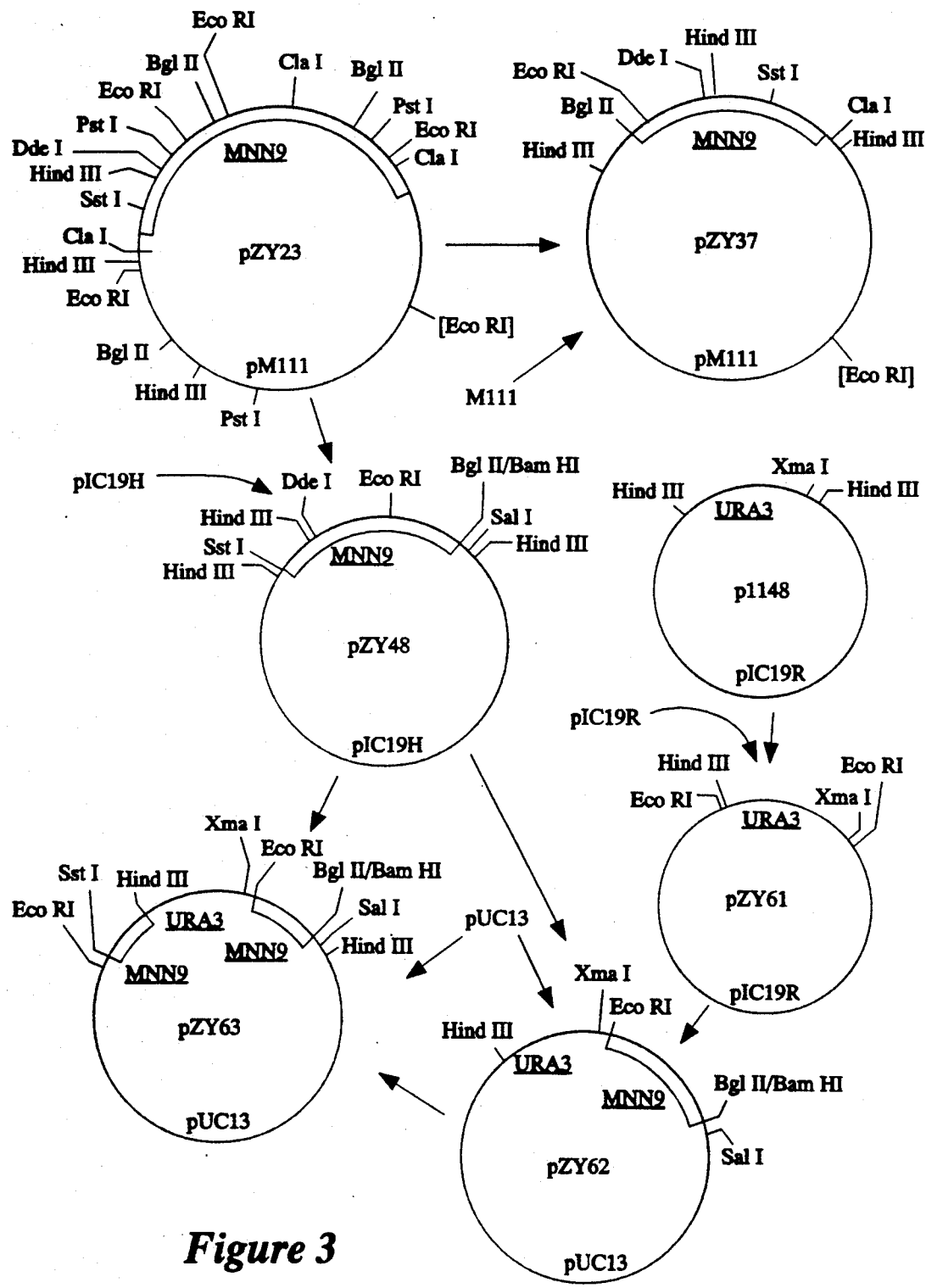
FIG. 3 illustrates the construction of pZY37, pZY48 and pZY63.

The plasmid with the smallest insert that restored the Mnn+ phenotype when transformed into mnn9 strains was designated pZY23. Plasmid pZY23 comprised a 6 kb yeast genomic DNA insert in pM111. Subclones of the genomic DNA insert present in pZY23 were made and used to transform strain XCY1-5D to check for complementation. As illustrated in FIG. 3, a subclone of pZY23 was made by digesting pZY23 with Cla I and Bgl II to isolate the 3.1 kb fragment comprising the MNN9 gene. The fragment was then ligated into pM111 which had been linearized by digestion with Cla I and Bgl II. The resultant plasmid pZY37 has been deposited as an *E. coli* strain RR1 transformant with the American Type Culture Collection (ATCC No. 67550). A 2.4 kb Bgl II-Sst I fragment of the cloned insert was found to be sufficient for complementation. This fragment was subcloned into pIC9H (Marsh et al., *Gene* 32:481-486, 1984; ATCC 37408) which had been linearized by digestion with Bam HI and Sst I. The resultant plasmid was designated pZY48 (FIG. 3).

D. Assay Methods.

Preparation of colonies

Appropriately grown cells were lysed by one of two methods. In the first method, colonies grown in YEPDS (Table 2) were treated with chloroform to permeabilize the cells. The plates were inverted (for 5 minutes at room temperature) onto paper towels which had been saturated with chloroform. The plates were then placed upright for 30 minutes to allow the chloroform to evaporate before assaying.

The second method was employed for colonies which required selective growth conditions on synthetic medium to maintain plasmids. Colonies that were grown on synthetic medium+1 M sorbitol were first transferred to nitrocellulose filters (Schleicher & Schuell, Keene, N.H.). Circular nitrocellulose filters were laid on top of colonies grown on synthetic medium +1 M sorbitol, until the filters were completely wetted. The filters were then carefully peeled away from the surface of the agar and dipped into liquid nitrogen for 30 seconds. This effectively lysed the cells. The filters were then paced cell-side up on YEPD plates (Table 2) for assaying.

Assay Method

Substrate was prepared as described below:

per plate:  2 ml 2% agar, melted, held at 55° C.
1 ml 0.5M NaH$_2$PO$_4$ pH 7.0, 55° C.
0.1 ml 20% sodium dodecylsulfate, 55° C.
6.4 ml dH$_2$O, 55° C.
0.5 ml 2 mg/ml cycloheximide (Sigma, St. Louis, Mo.)
100 mg azocoll (Sigma)

The azocoll does not dissolve. The mixture was swirled and quickly poured as an overlay over the colonies on the plate or filter.

The plates were incubated at 37° C. for 5-8 hours. Colonies exhibiting the Mnn9$^-$ phenotype were able to break down the azocoll immediately surrounding the colony resulting in a clear halo around mnn9 colonies.

EXAMPLE 2

Disruption of the MNN9 gene

In order to disrupt the MNN9 gene, a plasmid was constructed in which the URA3 gene replaced the coding region between the unique Hind III and Eco RI sites present in the MNN9 gene as illustrated in FIG. 3.

Plasmid p1148, comprising the 1.3 kb Hind III fragment encoding the URA3 gene (derived from YEp24; Botstein et al., *Gene* 8:17, 1979) in plasmid pIC19R, was digested with Hind III and Xma I to isolate the 1.1 kb URA3 fragment. This fragment was ligated into pIC19R which had been linearized by digestion with Hind III and Xma I. The resultant plasmid, pZY61, was digested with H nd III and Eco RI to isolate the 1.1 kb URA3 fragment. Plasmid pZY48 was digested with Eco RI and Sal I to isolate the 1.2 kb fragment encoding the 3' portion of MNN9. The fragment was joined with the URA3 fragment and pUC13, which had been linearized by digestion with Hind III and Sal I, n a three-part ligation. The resultant plasmid, pZY62, was digested with Hind III and Sal I to isolate the 2.3 kb fragment comprising the URA3 gene fused to the 3' portion of the MNN9 gene. Plasmid pZY48 was digested with Sst I and Hind III to isolate the 0.44 kb MNN9 fragment. This fragment was joined with the fragment from pZY63 and pUC13, which had been linearized with Sst I and Sal in a three-part ligation. The resultant plasmid, pZY63, comprised the MNN9 gene disrupted with the URA3 gene (FIG. 3).

The genomic MNN9 was disrupted in strains SEY2101 and ZY100 (Table 1) using the method described by Rothstein (ibid.). Plasmid pZY63 was digested with Sst I and Sal 1 to isolate the 2.7 kb fragment comprising the MNN9 coding region which has been disrupted with the URA3 gene. This fragment was transformed into yeast strains SEY2101 and ZY100. The transformants were selected for their ability to grow on UraDS plates (Table 2). Transformants were then assayed for the presence of a Mnn9− phenotype (Example 1.D.) which indicated the integration of the linear DNA fragment at the MNN9 locus. Positive clones were tested for the stability of the URA3 marker by growth on nonselective medium. Positive clones were inoculated into 5 ml YEPDS (Table 2) and grown overnight at 30° C. The overnight cultures were diluted 1 ul into 5 ml fresh YEPDS and were grown overnight at 30° C. The second overnight cultures were diluted 1 ul in 10 ml 1 M sorbitol. Ten ul of the mixture, added to 100 ul 1 M sorbitol, was plated on a YEPDS plate. These plates were incubated at 30° for 24 hours. The colonies were replica plated onto -UraDS to test for the stability of the URA3 marker. All the clones were stable.

Southern blot analysis was carried out on the transformants to confirm the integration event. Genomic DNA was prepared by the method described by Davis et al. (*Proc. Natl. Acad. Sci. USA* 802432-2436, 1983) and cut with Eco R1 and Sst I. The digests were electrophoresed in a 0.7% agarose gel and blotted onto a nitrocellulose filter according to the method described by Southern (ibid., 1975). The filter was probed with the 2.3 kb Hind III-Hind III fragment from pZY48, comprising the coding region of MNN9 (Example 1.C.) which was random primed with an Amersham random priming kit (Amersham, Arlington Hts., Ill.). A disruption in strain ZY100, designated ZY400, was confirmed by the presence of 1.5 and 1.55 kb labeled fragments on the Southern blot. A clone was isolated from the disruption in strain SEY2101, designated ZY300 (ATCC Accession No. 20870), which showed no gene disruption. Further experimentation confirmed the presence of a Mnn9− phenotype.

Pulsed-field gel electrophoresis (Southern et al., ibid., 1987 was carried out on genomic DNA derived from ZY300 and ZY400 and their parent strains. Genomic DNA was prepared using a method modified from the agarose bead method reported by Overhauser and Radic (*BRL Focus* 9:8-9, 1987). Briefly, overnight cultures were grown in 15 ml YEPDS at 30° C. The cultures were centrifuged, the supernatants were discarded and the pellets were resuspended in 5 mls SCE (1 M sorbitol, 0.1 M Na$_2$Citrate pH 5.8, 0.01 M Na$_2$EDTA pH 8.0). The cell suspensions were transferred to 50 ml Erlenmeyer flasks. 10 ml paraffin oil held at 55° C. and 1 ml 2.5% low-gelling agarose (Sea Plaque Agarose, FMC Corp. Bioproducts, Rockland, Me.) held at 55° C. were added to each flask. The cell slurries were mixed vigorously on a vortex at maximum speed for 1 minute until a fine emulsion was obtained. The emulsions were cooled rapidly, with swirling, in an ice-water bath. After cooling, the emulsions were transferred to 50 ml polystyrene tubes and 20 ml TE8 (10 mM Tris-HCl, 1 mM EDTA, pH 8.0) was added. The solutions were centrifuged at 2500 rpm for 5 minutes after which the paraffin oil and supernatants were discarded. The pellets, comprising the agarose beads, were resuspended n 30 m TE8 and centrifuged as described in the previous step. The supernatants were discarded and 5 ml spheroplasting buffer (for 2 ml of beads: 3 ml SCE, 2 ml 0.5 M EDTA (pH 9.0), 1 mg zymolyase 60,000 (Miles, Elkhart, Ind.), 0.25 ml β-mercaptoethanol (Sigma, St. Louis, Mo.) was added. The solutions were incubated at 37° C. for 1 hour on a rotating drum after which the solutions were centrifuged as previously described. The supernatants were discarded and replaced with 1 ml 0.5 M EDTA (pH 9.0) and stored at 4° C.

The yeast chromosomes were separated essentially as described by Southern et al. (ibid., 1987). Pulsed-field gel electrophoresis, in a 1% agarose ge, (Seakem Agarose, FMC Corp. Bioproducts, Rockland, Me.) was performed using a Rotogel (Moonlight Cat Door Company, Seattle, Wash.). Yeast DNA was visualized by staining with ethidium bromide. Analysis of the stained gel revealed that strain ZY300 had undergone chromosome rearrangement involving at least chromosomes V and VIII. A Southern blot was made of the gel as previously described, and probed first with the 2.3 kb Hind III-Hind III MNN9 fragment derived from pZY48 and then with the 1.3 kb Hind III-Hind III URA3 fragment derived from p1148 (Example 2). The probes were labeled using the Amersham random priming kit (Amersham, Arlington Hts., Ill.). Results of the Southern blot showed that in both ZY300 and ZY400, all of the MNN9 coding region, mapped to chromosome XVI (the natural site for MNN9) and URA3 mapped to chromosomes XVI and V as expected.

EXAMPLE 3

Expression of Barrier in mnn9 deletion strains

Figure 5:
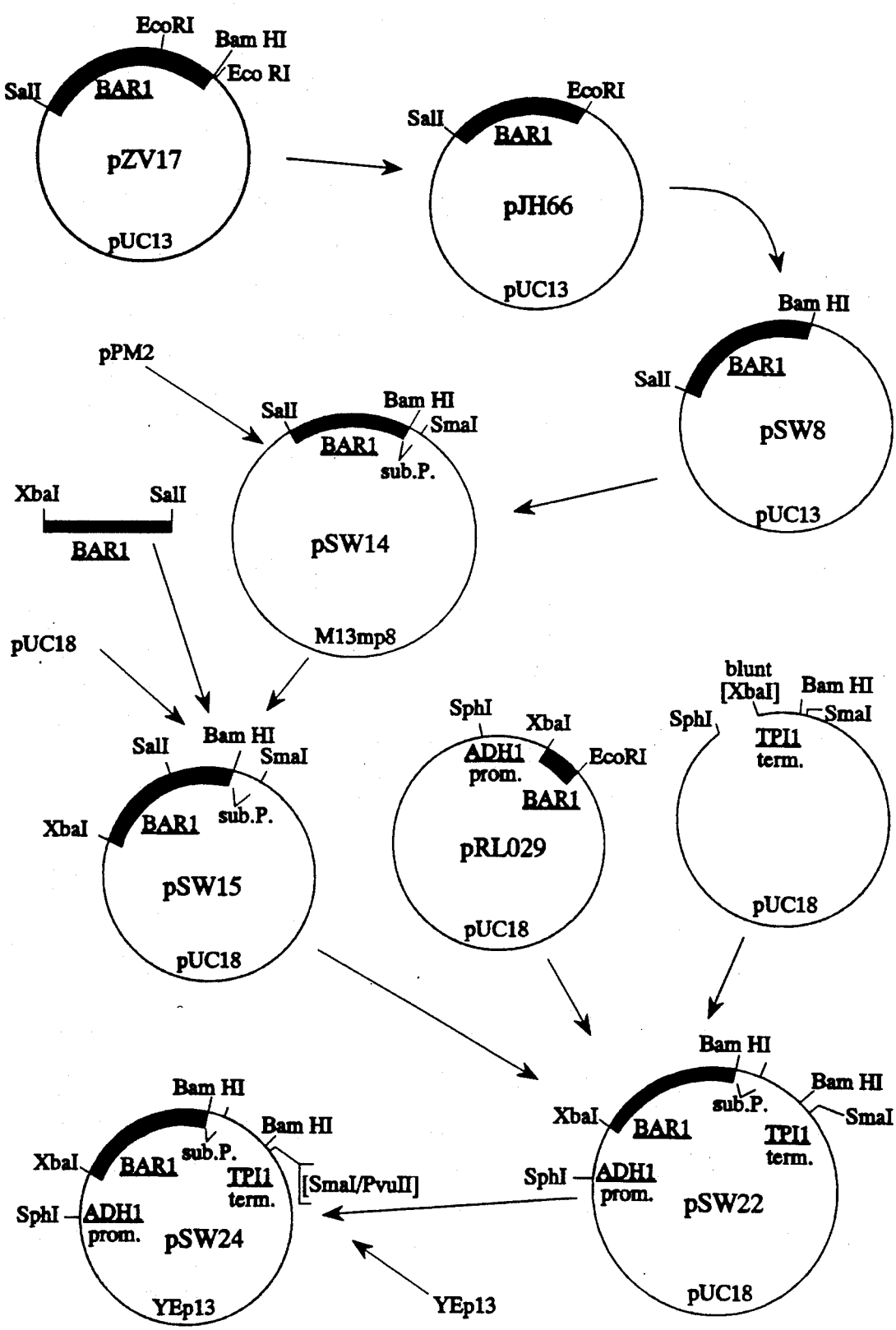
FIG. 5 illustrates the construction of pSW24.

A DNA construct comprising the BAR1 gene was transformed into the mnn9 deletion strains generated in Example 2 and their parent strains to examine the glycosylation of the Barrier protein. The BAR1 gene product, Barrier, is an exported protein which has been shown to be highly glycosylated. Plasmid pSW24, comprising the ADH1 promoter, the BAR1 coding region fused to the coding region of the C-terminal portion of substance p (Munro and Pelham, *EMBO J.* 3:3087-3093, 1984) and the TPI1 terminator, was constructed as follows (FIG. 5). Plasmid pZV9, comprising the entire BAR1 coding region and its associated flanking regions, was cut with Sal I and Bam HI to isolate the 1.3 kb BAR1 fragment. This fragment was subcloned into pUC13 cut with Sal I and Bam HI to generate the plasmid designated pZV17 (FIG. 4). plasmid pZV17 was digested with Eco RI to remove the 3'-most 0.5 kb of the BAR1 coding region. The vector-BAR1 fragment was religated to create the plasmid designated pJH66. Plasmid pJH66 was linearized with Eco RI and blund-ended with DNA polymerase I (Klenow fragment). Kinased Bam H linkers (5'CCGGATCCGG3') were added, and excess linkers were removed by digestion with Bam HI before re-ligation. The resultant plasmid was designated pSW8. Plasmid pSW8 was cut with Sal I and Bam HI to isolate the 824 bp fragment encoding amino acids 252 through 526 of Barrier. Plasmid pPM2, containing the synthetic oligonucleotide sequence encoding amino acids 252 through 526 of Barrier. Plasmid pPM2, containing the synthetic oligonucleotide sequence encoding the dimer form of the C-terminal portion of substance P in M13mp8, was obtained from Munro and Pelham. Plasmid pPM2 was linearized by digestion with Bam HI and Sal I and ligated with 824 bp BAR1 fragment from pSW8. The resultant plasmid, pSW14, was digested with Sal I and Sma I to isolate the 871 bp BAR1-substance P fragment. Plasmid pZV16, comprising a fragment of BAR1 encoding amino acids 1 through 250, was cust with Xba I and Sal I to isolate the 767 bp BAR1 fragment. This fragment was ligated with the 871 bp BAR1-substance P fragment in a three-part ligation with pUC18 cut with Xba I and Sma 1. The resultant plasmid, designated pSW15, was digested with Xba I and Sma I to isolate the 1.64 kb BAR1-substance P fragment. The ADH1 promoter was obtained from pRL029, comprising the ADH1 promoter and the 116 bp of the BAR1 5' coding region in pUC18 (MacKay, WO 87/02670). Plasmid pRL029 was digested with Sph I and Xba I to isolate the 0.42 kb ADH1 promoter fragment. The TPI1 terminator (Alber and Kawasaki, *J. Mol. Appl. Genet.* 1:410–434, 1982) was provided as a blunted Xba I-Sph I fragment comprising 0.7 kb of the TPI1 terminator (blunted Xba I to Eco R1) linked to pUC18 (Eco RI-Sph I). This fragment was ligated with the 0.42 kb ADH1 promoter fragment and the 1.64 kb BAR1-substance P fragment in a three-part ligation to produce plasmid pSW22. Plasmid pSW22 was digested with Sph I and Sma I to isolate the 2.8 kb expression unit which was lgated into YEp13 which had been linearized by digestion with Sph I and Pvu II. The resultant plasmid was designated pSW24 (FIG. 5).

Plasmid pSW24 was transformed into the mnn9 deletion strains pZY300 and pZY400 and their parent strains SEY2101 and pZY100. Transformants were selected for their ability to grow on -LeuDS plates (Table 2). Transformants were inoculated into 5 ml -LeuDS (Table 2) and incubated overnight at 30° C. Five hundred ul of the overnight cultures were inoculated into 50 ml -LeuDS and incubated for 48 hours at 30° C. The cultures were centrifuged, and the supernatants were decanted into 250 ml centrifuge bottles. An equal volume of 95% ethanol, held at −20° C., was added and the mixtures were vortexed and incubated at −20° C. for 30 minutes. The mixtures were then centrifuged at 9,000 rpm for 30 minutes in a SA (Sorvali) rotor. The supernatants were discarded and the protein pellets were allowed to dry overnight at room temperature. The dried pellets were resuspended in 500 ul dH2O.

Fifty ul of 2X sample buffer (Table 3) was added to each of the resuspended samples and the samples were electrophoresed in a 10% polyacrylamide gel and transferred to nitrocellulose using the method described by Towbin et al. (*Proc. Natl. Acad. Sci. USA* 76:4350–4353, 1979). The nitrocellulose filter was probed with rat anti-substance P (Capell, Malvern, Pa.) and visualized using horseradish peroxidase-conjugated goat anti-rat antibodies. The immunoblot showed a homogeneous species recognized by the anti-substance P antibody in the mnn9 disruption strains ZY300 and ZY400, indicating that the Barrier protein produced by these strains is homogeneous. Parental strains showed a heterogeneous, hyperglycosylated species which was recognized by the anti-substance P antibody.

The pSW24 transformants were assayed for Barrier activity as follows. The assay used for detection of Barrier production by transformed yeast cells relies on the ability of Barrier to reverse the inhibition of growth of sensitive a cells exposed to α-factor. A lawn was prepared using a test strain, such as strain RC629 (MATa -bar1) which is abnormally sensitive to a-factor, in a soft agar overlay on an agar plate. A sufficient quantity of α-factor (0.05–0.1 unit, as assayed by Manney, *J. Cell Biol.* 96:1592–1600, 1983) was added to the overlay to inhibit growth of the cells. Transformants to be screened for Barrier production were spotted onto the lawn. Secretion of Barrier by the transformed cells reversed the α-factor growth inhibition immediately surrounding the spot, thereby allowing the sensitive cells to recover. The recovered cells were observed as a fringe of growth around the normally smooth edge of the colony of transformed cells. The presence of this fringe indicated that the plasmid in the transformed strain directed the expression and secretion of Barrier protein. The transformants were shown to make active Barrier protein.

EXAMPLE 4

Expression of tissue plasminogen activator from mnn9 deletion strains

A DNA construct comprising the tissue plasminogen activator (tPA) cDNA was transformed into the mnn9. deletion strain ZY400 to examine the glycosylation of the protein produced. Plasmid pDR1498 (deposited as a yeast transformant in strain E8-11C, ATCC #20730), comprising the TPI1 promoter, the MFα1 signal sequence fused to the serine codon of the mature tPA cDNA sequence and the TPI1 terminator, was transformed into strain ZY400 and its parent, ZY100. Transformants were selected for their ability to grow on -LeuDS plates (Table 2).

Transformants were grown as described in Example 3. After 48 hours of growth at 30° C., the cultures were split into 25 ml aliquots and centrifuged. The supernatants from one set of 25 ml aliquots were decanted and saved at −70° C. Their respective pellets were also saved at −70° C.

Cell extracts were made on the remaining cell pellets in the following manner. One ml Phosphate Buffered Saline (PBS; obtained from Sigma, St. Louis, Mo.)+1 mM EDTA was added to one-half the total volume. The mixtures were vortexed at full speed for 2.5 minutes, three times with the samples cooled on ice between vortex bursts. The lysates were centrifuged in an Eppendorf microfuge (Brinkmann, Westbury, N.Y.) at top speed for 10 minutes at 4° C. The supernatants, comprising soluble cell proteins, were removed and stored at −70° C. The pellets were washed with 1 ml 2X TNEN (100 mM Tris-Base, 200 mM NaCl, 1 mM EDTA, 0.5% NP-40, adjusted to pH 8.0). The mixtures were vortexed and centrifuged as previously described. The supernatant, comprising the membrane protein fraction, was removed and stored at −70° C.

EXAMPLE 5

Temperature-Regulated MNN9 gene

The TPI1 promoter was obtained from plasmid pTPIC10 (Alder and Kawasaki, *J. Mol. Appl. Genet.* 1:410-434, 1982), and plasmid pFATPOT (Kawasaki and Bell, EP 171,142; ATCC 20699). Plasmid pTP1C10 was cut at the unique Kpn I site, the TPI1 coding region was removed with Bal-31 exonuclease, and an Eco RI linker (sequence: GGAATTCC) was added to the 3' end of the promoter. Digestion with Bgl II and Eco RI yielded a TPI1 promoter fragment having Bgl II and Eco RI sticky ends. This fragment was then joined to plasmid YRp7" (Stinchcomb et al., *Nature* 282:39–43, 1979) which had been cut with Bgl II and Eco RI (partial). The resulting plasmid, TE32, was cleaved with Eco RI (partial). The resulting plasmid, TE32, was cleaved with Eco RI (partial) and the Bam HI to remove a portion of the tetracycline resistance gene. The linearized plasmid was then recircularized by the addition of an Eco RI-Bam HI linker to produce plasmid TEA32. Plasmid TEA32 was digested with Bgl II and Eco RI, and the ~900 bp partial TPI1 promoter fragment was gel-purified. Plasmid pIC19H (Marsh et al., *Gene* 32:481-486, 1984) was cut with Bgl II and Eco RI and the vector fragment was gel-purified. The TPI1 promoter fragment was then ligated to the linearized PIC19H and the mixture was used to transform *E. coli* RR1. Plasmid DNA was prepared and screened for the presence of a ~900 bp Bgl II-Eco RI fragment. A correct plasmid was selected and designated pICTPIP.

The TPI1 promoter was then subcloned to place convenient restriction sites at its ends. Plasmid pIC7 (Marsh et al., ibid.) was digested with Eco RI, the fragment ends were blunted with DNA polymerase I (Klenow fragment), and the linear DNA was recirculized using T4 DNA ligase. The resulting ligation mixture was used to transform *E. coli* RR1. Plasmid DNA was prepared from the transformants and screened for the loss of the Eco RI site. A plasmid having the correct restriction pattern was designated pIC7RI*. Plasmid pIC7RI* was digested with Hind III and Nar I, and the 2500 bp fragment was gel-purified. The partial TPI1 promoter fragment (ca. 900 bp) was removed from pICTPIP using Nar I and Sph I and was gel-purified. The remainder of the TPI1 promoter was obtained from plasmid pFATPOT, by digesting the plasmid with Sph I and Hind III and a 1750 bp fragment, which included a portion of the TPI1 promoter, was gel-purified. The pIC7RI* fragment, the partial TPI1 promoter fragment from pICTPIP, and the fragment from pFATPOT were then combined in a triple ligation to produce pMVR1 (FIG. 6).

Figure 6:
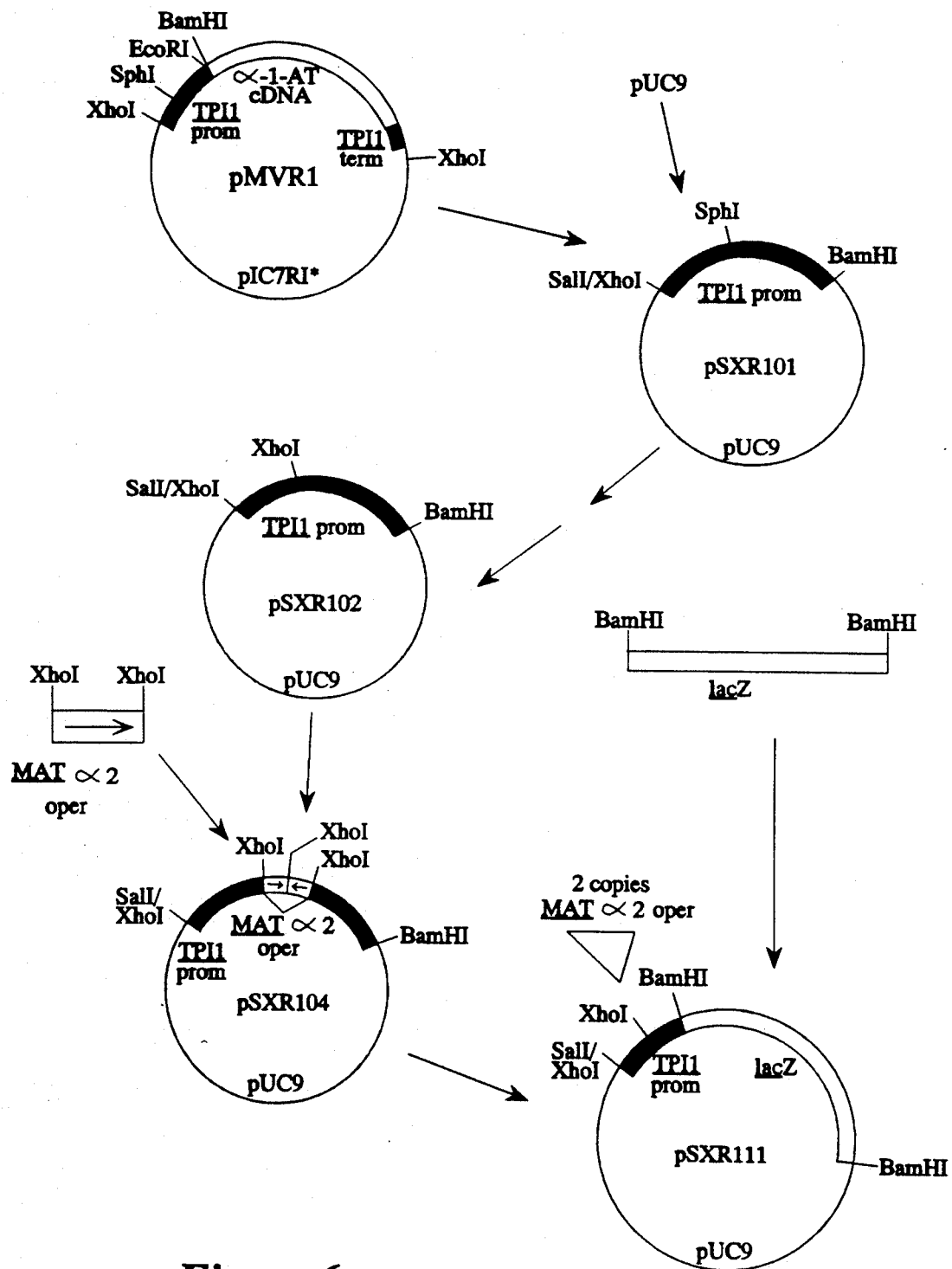
FIG. 6 illustrates the construction of pSXR111.

As shown in FIG. 6, the MATα2 operator sequence was then inserted into the TPI1 promoter. Plasmid pSXR101 was constructed by ligating the 2.7 kb Sal I-Bam HI fragment of pUC9 with 0.9 kb Xho *-Bam HI fragment of the TPI1 promoter derived from plasmid pMVR1. The Sph I site of the TPI1 promoter in plasmid pSXR101 was then changed to a unique Xho I site. pSXR101 DNA was cleaved with Sph I and dephosphorylated according to standard procedure (Maniatis et al., eds., *Molecular Cloning: A Laboratory Manual*, Cold Spring, N.Y., 1982). An Sph I-Xho I adaptor (GCTCGAGCCATG) was kinased in a separate reaction containing 20 pmoles of the oligonucleotide, 50 mM Tris-Hcl, pH 7.6, 10 mM MgCl2, 5 mM DTT, 0.1 mM spermidine, 1 mM ATP, and 5 units of polynucleotide kinase in a reaction volume of 20 ul for 30 minutes at 37° C. The kinased Sph I-Xho I adaptor was ligated with Sph I-cut pSXR101, and the ligation mixture was used to transform *E. coli* RR1. Plasmids with inserted adaptor were identified by restriction analysis and named pSXR102 (FIG. 6). The oligonucleotides specifying the MATα2 operator (element 609: 5' TCGAG TCA TGT ACT TAC CCA ATT AGG AAA TTT ACA TGG 3' and 5' TCGA CCA TGT AAA TTT CCT AAT TGG GTA AGT ACA TGA C 3') were kinased as described above. Plasmid pSXR102 was cut with XHO I and dephosphorylated according to standard procedures. Three independent ligations were set up, with molar ratios of plasmid DNA to oligonucleotide of 1:1, 1:3 and 1:6, respectively. The resultant ligation mixtures were used to transform *E. coli* RR1. Plasmids with inserted oligonucleotide(s) were identified by colony hybridization and restriction analysis. Subsequent DNA sequencing showed the pSXR104 contained two copies of the MATα2 operator.

In the next step, plasmid pSXR104 was cut with Bam HI, dephosphorylated according to standard procedure (Maniatis et al., eds. in *Molecular Cloning: A Laboratory Manual*, Cold Spring Harbor, N.Y., 1982), and ligated with a 3.2 kb Bam Hi-Bam Hi fragment comprising the *E. coli* lacZ gene. The ligation mixture was used to transform *E. coli* strain RR1. A plasmid containing the lacZ fragment in the appropriate orientation was designated pSXR111.

Figure 7:
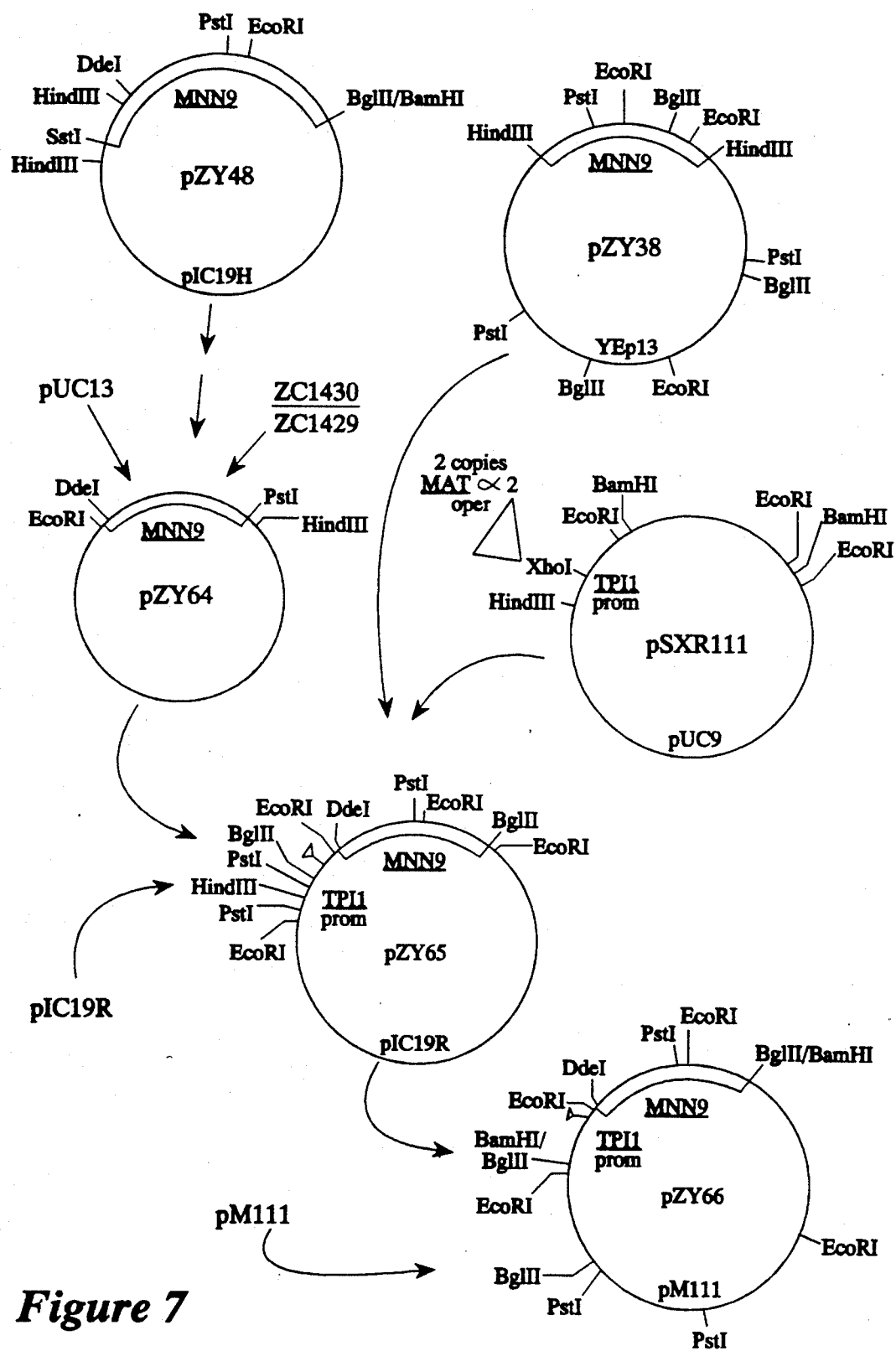
FIG. 7 illustrates the construction of pZY66.

As illustrated in FIG. 7, the MNN9 gene was placed under the regulation of the hybrid promoter present in plasmid pSXR111. Plasmid pZY48 was digested with Hind III and Pst I to isolate the 0.56 kb MNN9 fragment. This fragment was cut with Dde I to isolate the 0.36 kb MNN9 fragment. Oligonucleotides ZC1429 (5' TTA GGC GGT ACG ATA CAA GAG AAA GTG ACA TTG TTT CCT G 3') and ZC1430 (5' AAT TCA GGA AAC AAT GTC ACT TTC TCT TGT ATC GTA CCG CC 3') were kinased and annealed using methods essentially described by Maniatis et al. (ibid.). The kinased, annealed oligonucleotides create an adaptor with an Eco RI cohesive end followed by 37 bp of MNN9 coding region and a Dde I cohesive end. The ZC1429/ZC1430 adaptor was joined to the Dde I-Pst I fragment from pZY48 in a three-part ligation with pUC13 which ad been linearized by digestion with Eco RI and Pst I. The resultant plasmid, comprising the ZC1429/ZC1430 adapter fused to the MNN9 gene, was designated pZY64.

Plasmid pZY64 was digested with Eco RI and Pst 1 to isolate the 0.4 MNN9 fragment. Plasmid pZY38, comprising the 1.5 kb Pst I-Bgl II fragment from pZY23 and YEp13 vector sequences, was digested with Pst I and Bgl II to isolate the 1.5 kb MNN9 fragment. Plasmid pSXR111 was digested with Hind III and Eco RI to isolate the 0.9 kb hybrid promoter fragment. This fragment was ligated in a four-part ligation with the 1.5 kb Pst I-Bgl II fragment from pZY38, the Eco RI-Pst I fragment from pZY64 and pIC19R which had been linearized by digestion with Hind III and Bgl II. The resultant plasmid was designated pZY65. Plasmid pZY65 was digested with Bgl II and Pvu 1. The 2.8 kb Bgl II-Bgl II fragment comprising the expression unit was isolated. Plasmid pM111 was linearized by digestion with Bam HI and ligated with the 2.8 kb Bgl II fragment comprising the expression unit from pZY65. The resultant ligation mix was transformed into *E. coli* strain RR1. Plasmid DNA was made from the transformants and cut with Hind III and Eco RI to determine the orientation of the insert. A plasmid with the expression unit in the correct orientation was designated pZY66.

EXAMPLE 6

Expression of the Temperature-Regulated MNN9 gene.

A. Construction of Strain XCY42-28B.

A *S. cerevisiae* strain having the sir3-8 mutation, a deletion in the MNN9 gene and genetic defects in at least LEU2 and TRP1 genes was constructed as follows. (Genotypes of all strains are listed in Table 1.) Strain 381G-59A (Hartwell, *J. Cell Biol* 85:811–822, 1980) was crossed with strain A2 (Ruby et al., *Meth. Enzymo.* 101:253–269, 1983) and diploids were selected and sporulated. Asci were dissected and a spore with the genotype MATa leu2-3,112 trp1-1 ade2-1 lys2 sir3-8 was designated XL1-4B. Strains ZY400[pSW24]and ZA447 were crossed and diploid cells were selected. Diploid cells were sporulated using conventional methods and asci were dissected. Tetrad analysis was carried out on the resultant spores. A spore was selected having the genotype MATα ade2-1 leu2-3,112 Δmnn9::URA3. The spore was designated XCY15-3C.

Strains XCY15-3C and XL1-4B were crossed to generate the diploid XCY42. This diploid strain was sporulated and asci were dissected. A spore was chosen which had the genotype of MATα sir3-8 Δmnn9::URA3 leu2-3,112 trp1-1 ade2-1 lys2. This spore was designated XCY42-28B. Strain XCY42-28B has been deposited with the American Type Culture Collection under Accession No. 20877.

B. Production of polyclonal antibodies directed against a trpE-BAR1 fusion.

Polyclonal antibodies were raised against a trpE-Barrier protein. The trpE-Barrier protein was produced from *E. coli* RR1 which had been transformed with pSW242. Plasmid pSW242 was constructed as follows. Plasmid pSW22 (Example 3) was digested with Eco RI to isolate the 1.47 kb BAR1 fragment. Plasmid pATH11 (Morin et al., *Proc. Natl. Acad. Sci. USA* 82:7025–7029, 1985; a variant of pATH2 [Dieckmann and Tzagoloff, *J. Biol. Chem.* 260:1513–1520, 1985], in which a portion of the *E. coli* trpE gene is followed by a multiple cloning region and vector sequences of a pUC type plasmid) was linearized by digestion with Eco RI. The two Eco RI fragments were joined by ligation and transformed into *E. coli* strain RR1. Plasmid DNA made from the transformants was screened by restriction analysis and a clone containing the BAR1 fragment in the appropriate orientation was designated pSW242.

A transformant colony of *E. coli* RR1 harboring plasmid pSW242 was inoculated into 4 ml of M9+CA+amp+W (Table 2) and grown overnight at 37° C. The overnight culture was diluted 1:10 in 30 ml M9+CA+amp (Table 2) and grown for 1 hour at 30° C. with great aeration. After 1 hour 150 ul of 10 mg/ml indoleacrylic acid (Sigma, St. Louis, Mo.) in 100% ethanol was added to the culture and it was grown for an additional 2 hours at 30° C.

TABLE 3

2 × Sample Buffer
36 ml 0.5M Tris-HCl, pH 6.8
16 ml glycerol
16 ml 20% SDS
4 ml 0.5% Bromophenol Blue in 0.5M Tris-HCl, pH 6.8
Mix all ingredients. Immediately before use, add
100 ul β-mercaptoethanol to each 900 ul dye mix.
Cracking Buffer
0.01M sodium phosphate, pH 7.2
1% β-mercaptoethanol
1% sodium dodecylsulfate
6M urea
Western Transfer Buffer
25 mM Tris, pH 8.3
19 mM glycine, pH 8.3
20% methanol
Western Buffer A
50 ml 1M Tris, pH 7.4
20 ml 0.25 mM EDTA, pH 7.0
5 ml 10% Np-40
37.5 ml 4M NaCl
2.5 g gelatin The Tris, EDTA, NP-40 and NaCl were diluted to a final volume of one liter with distilled water. The gelatin was added to 300 ml of this solution and the solution was heated in a microwave oven until the gelatin was dissolved into solution. The gelatin solution was added back to the remainder of the first solution and stirred at 4° C. until cool. The buffer was stored at 4° C.

Western Buffer B 50 ml 1 M Tris, pH 7.4
20 ml 0.25 M EDTA, pH 7.0
5 ml 10% NP-40
58.4 g NaCl
2.5 g gelatin
4 g N-lauroyl sarcosine The Tris, EDTA, NP-40 and NaCl were mixed and diluted to a final volume of one liter. The gelatin was added to 30 ml of this solution and heated in a microwave oven until the gelatin was dissolved into solution. The gelatin solution was added back to the original solution and the N-lauroyl sarcosine was added. The final mixture was stirred at 4° C. until the solids were complete)y dissolved. This buffer was stored at 4° C.

The culture was pelleted by centrifugation and the supernatant was discarded. The cell pellet was resuspended in 50 ul cracking buffer (Table 3) and incubated at 37° C. for 0.5-3 hours. An equal volume of 2×sample buffer (Table 3) was added and the sample was heated in boiling water bath for 3-5 minutes. The sample was electrophoresed in a 10% SDS-polyacrylamide gel. The proteins were transferred to nitrocellulose using the method essentially described by Towbin et al. (ibid.). The nitrocellulose filter was stained by immersion in a solution of 100 ml distilled water, 4 ml glacial acetic acid and 4 drops Schilling green food coloring (McCormick and Co., Inc., Baltimore, Md.). The band corresponding to Barrier protein was cut out of the filter and the stain was removed by a distilled water wash. The de-stained nitrocellulose filter containing the Barrier protein was dried at 37° C. for one hour and was subsequently mixed with Freund's adjuvant (ICN Biochemicals, Costa Mesa, Calif.) and dimethyl sulfoxide (DMSO). The mixture was injected subcutaneously at three sites into New Zealand White rabbits. The injections were repeated 2.5 months after the first injection. Ten days after the final injection, whole blood was removed from the rabbit and allowed to coagulate. The blood clot was separated from the serum by centrifugation. The serum was removed to a fresh tube and stored at −20° C. These polyclonal antibodies, designated C-2465, recognized the Barrier protein.

C. Expression of BAR1 in a temperature regulated MNN9 strain

*S. cerevisiae* strain XCY42-28B was transformed with the temperature regulated MNN9 expression vector pZY66 (Example 5) and pSW24 (Example 3) or with pSW24 and pM111 using methods known in the literature, see for example, Beggs (ibid.). Transformants were selected for their ability to grow on -Leu-TrpDS (Table 2) at 25° C.

Transformants were streaked for single colonies on -Leu-TrpDS plates and were grown at 25° C., 30° C. or 35° C. Transformant colonies were inoculated into 5 ml -Leu-TrpDS and were grown overnight at 25° C., 30° C. or 35° C., depending on the growth temperature of the inocula. The overnight cultures were diluted 1:100 in 50 m -Leu-TrpDS and grown for approximately 48 hours at 25° C., 30° C. or 35° C.

The cells were removed from the culture by centrifugation and the supernatants were decanted and saved. An equal volume of 95% ethanol, held at −20° C., was added to each supernatant and the mixtures were kept at −20° C. for 45 minutes. The ethanol mixtures were spun in a GSA (Sorval) rotor at 9,0000 rpm for 30 minutes at 4° C. to pellet the precipitate. The supernatants were decanted and the pellets were allowed to dry. The pellets were resuspended in 500 ul distilled water.

Fifty ul of 2×sample buffer (Table 3) was added to 50 ul of each resuspended sample and the mixture was electrophoresed in a 10% polyacrylamide gel and transferred to nitrocellulose using the method essentially described by Towbin et al. (ibid.). The nitrocellulose filter was probed with the rabbit polyclonal C-2465 and visualized using horseradish peroxidase-conjugated goat anti-rabbit antibodies. The immunoblot showed that at 35° C., the Barrier-substance P protein made by XCY42-28B[pSW24, pZY66] was present as a homogeneous species which carried the same amount of glycosylation as XCY42-28B[pSW24, pM111] grown at all temperatures. This indicated that at 35° C. the MNN9 gene is turned off and protein glycosylation is carried out as is found in a similarly transformed mnn9 strain. At 30° C., the Barrier-substance P protein produced from XCY42-28B[pSW24, pZY66]was mostly hyperglycosylated and at 25° C., the Barrier-substance P protein produced from XCY42-28B[pSW24, pZY66-]was a very heterogeneous hyperglycosylated species.

EXAMPLE 7

A Method to Detect mnn1 Mutants

Rabbit polyclonal antibodies were raised against Barrier protein which was produced from a mnn9 strain. Barrier protein was produced from XV732-1-9A (Example 1.A.) which had been transformed with pZV100, comprising the TPI1 promoter, MFα1 signal sequence, and the BAR1 coding sequence. Plasmid pZV100 was constructed as follows.

The TPI1 promoter was derived from plasmid pM210 (also known as pM220, which has been deposited with ATCC Accession No. 39853). plasmid pM210 was digested with Bgl II and Hind III to isolate the 0.47 kb fragment (fragment 1).

A Hind III-Eco RI adaptor encoding the MFα1 signal peptide was subcloned with a portion of the 5' coding sequence of the BAR1 gene deleted for the putative BAR1 signal sequence into the cloning vector pUC13. Plasmid pZV16 (Example 3) was digested with Eco RI and Sal I to isolate the 0.67 kb BAR1 fragment. Oligonucleotides ZC566 (5' AGC TTT AAC AAA CGA TGG CAC TGG TCA CTT AG 3') and ZC567 (5' AAT TCT AAG TGA CCA GTG CCA TCG TTT GTT AA 3') were kinased and annealed essentially as described in Maniatis et al. (ibid.). The kinased, annealed ZC566/ZC567 adaptor was joined with the 0.67 kb BAR1 fragment in a three-part ligation with pUC13 which had been linearized by digestion with Hind III and Sal I. The resultant ligation mixture was transformed into *E. coli* strain JM83. plasmid DNA made from the resultant transformants were screened by digestion with Hind III and Sal 1. A positive clone was designated plasmid pZV96. Plasmid pZV96 was digested with Hind III and Sal I to isolate the 0.67 kb fragment comprising the ZV566/ZC567 adaptor-BAR1 fragment (fragment 2).

The remainder of the BAR1 gene was derived from pZV9 (Example 3). Plasmid pZV9 was digested with Sal I and Bam HI to isolate the 1.25 kb BAR1 fragment (fragment 3). Fragments 1 and 2 (comprising the TPI1 promoter-MFα1 signal sequence and the ZC566/ZC567-BAR1 fragment, respectively) were joined with fragment 3 (1.25 kb BAR1 fragment) and YEp13 which had been linearized by digestion with Bam HI. The resultant ligation mixture was transformed into *E. coli* RR1. Plasmid DNA made from the resultant transformants was digested with Bam HI+Hind III and Bam HI+Sal I to confirm the construction and to determine the orientation of the insert. A positive clone having the TPI1 promoter proximal to the Hind III sites on the YEp13 vector was designated pZV100.

*S. cerevisiae* strain XV732-1-9A was transformed with pZV100 and transformants were selected for their ability to grow on -LeuDS plates (Table 2). A transformant colony was inoculated into 10 m -LeuDS (Table 2) and was grown overnight at 30° C. The overnight culture was diluted 1:100 into 978 ml -LeuDS and the culture was grown for 43 hours at 30° C. The culture was centrifuged and the supernatants were decanted into 250 ml centrifuge bottles. An equal volume of 95% ethanol, held at −20° C., was added and the mixtures were incubated at −20° C. for approximately 2 hours. The mixtures were centrifuged in a GSA (Sorval) rotor at 9,000 rpm for 30 minutes at 4° C. The supernatants were discarded and the protein pellets were allowed to air dry. The pellets were resuspended in a total volume of 6 ml of 1× sample buffer (3 ml dH$_2$O and 3 ml 2×sample buffer [Table 2]).

The sample was electrophoresed in a 10% polyacrylamide gel and was transferred to nitrocellulose using the method described by Towbin et al. (ibid). The nitrocellulose filter was stained by immersion in a solution of 100 ml distilled water, 4 ml glacial acetic acid, and 4 drops Schilling green food coloring. The band corresponding to Barrier protein was cut out of the filter and the stain was removed by a distilled water wash. The de-stained nitrocellulose-Barrier band was dried at 37° C. for one hour and was subsequently mixed with Freund's adjuvant (ICN Biochemicals, Costa Mesa, Calif.) and dimethyl sulfoxide (DMSO). The mixture was injected subcutaneously at three sites into New Zealand White rabbits. The injections were repeated a total of three times at approximately one-month intervals. Ten days after the final injection, whole blood was removed from the rabbit and allowed to coagulate. The blood clot was separated from the serum by centrifugation. The serum was removed to a fresh tube and stored at −20° C. These polyclonal antibodies recognized the Barrier protein and the sugar moieties present on the protein.

Colonies of test strains were grown on YEPDS and the resultant colonies were replica plated onto nitrocellulose filters. The filters were subjected to three fifteen-minute washes in Western Transfer Buffer A (Table 3). The filters were then washed in Western Buffer A (Table 3) for five minutes. The filters were transferred to fresh Western Buffer A and incubated for one hour. The filters were then washed with Western Buffer A for five minutes. A 1:500 dilution of the rabbit polyclonal anti-Barrier (mnn9) antibody was added to the filters and incubated for longer than one hour. Excess antibody was removed by three fifteen-minute washes in Western Buffer A. A 1:1000 dilution of goat anti-rabbit horseradish peroxidase-conjugated antibody was added to the filters, which were incubated for at least one hour. Excess conjugated antibody was removed with a distilled water rinse followed by three ten-minute washes with Western Buffer B (Table 3) and a final distilled water rinse. The assay was developed by the addition of horseradish peroxidase substrate (BioRad, Richmond, Calif.) which was allowed to develop until there was sufficient color generation. Colonies which were lightly stained with the antibodies were mnn1 colonies.

EXAMPLE 8

Construction of mnn1 and mnn1 mnn9 strains

S. cerevisiae strains carrying mnn1 and mnn1 mnn9 mutations were constructed as follows. ZY400 (Table 1) was crossed with LB1-22D (Table 1, Yeast Genetic Stock Center, Berkeley, Calif.), and a diploid was selected and designated XV803. XV803 diploid cells were sporulated and asci were dissected. Spores were screened for the presence of the mnn1 mutation using the mnn1 screening method. The Δmnn9::URA3 marker was scored by the growth of the spores on YEPD (mnn9 mutants grow poorly on medium without osmotic support). A spore whose genotype was MATα leu2-3,112 Δmnn9::URA3 mnn1 was designated XV803-18. Another spore whose genotype was MATα leu2-3,112 mnn1 Δpep4::CAT was designated XV803-16C.

EXAMPLE 9

Expression of BAR1 in a mnn1 mnn9 strain

The expression of the BAR1 gene was examined in mnn1 mnn9 strains. Strains XV803-16C, XV803-16C, XY100 and ZY400 were transformed with pSW24. The transformants were selected for their ability to grow on -LeuDS plates (Table 2). Transformant colonies were streaked for single colonies onto fresh -LeuDS plates and allowed to grow at 30° C. Transformant colonies were inoculated into 50 ml -LeuDS (Table 2) and grown at 30° C. for approximately 48 hours. The cultures were harvested and the cells were removed from the culture media by centrifugation. The supernatants were decanted into GSA bottles and equal volumes of 95% ethanol, held at −20° C., were added. The mixtures were incubated at −20° C. followed by centrifugation in a GSA rotor at 9000 rpm for 30 minutes at 4° C. The supernatants were discarded and the precipitates were allowed to air dry. The precipitates were resuspended in 4 ml distilled water and were re-precipitated by the addition of 4 ml of cold 95% ethanol. The mixtures were incubated and centrifuged as describe above. The supernatants were discarded and the pellets were allowed to air dry.

The protein precipitates were resuspended in 150 ul distilled water. The samples were diluted with 150 ul 2× sample buffer (Table 3), and 100 ul of each sample was then electrophoresed in a 10% polyacrylamide gel. The proteins were transferred to nitrocellulose by the method of Towbin et al. (ibid.) and the Barrier protein was visualized using the substance P antibody, as described in Example 3. The results showed that the Barrier protein made from the mnn1 mnn9 double mutant ran faster than the Barrier protein isolated from a mnn9 or mnn1 mutant, indicating that the Barrier protein made from the double mutant contained fewer sugar moieties than the protein made from the mnn9 mutant.

EXAMPLE 10

Cloning the MNN1 gene

The MNN1 gene is cloned using the antibody screening method described above. A library of plasmids containing a random mixture or total yeast DNA fragments cloned into the vector YEp13 (Nasmyth and Reed, Proc. Natl. Acad. Sci. USA 77:2119–2123, 1980) is transformed into strain XV803-16C, and transformants are selected for their ability to grow on -LeuDS plates (Table 2). Transformants are resuspended in -LeuD (Table 2) by the method of MacKay (ibid., 1983) and counted. The pools are diluted and plated on -LeuD plates (Table 2) at a density of approximately 1200 cells/plate (if all the cells are viable). The plates are incubated at 30° C. until colonies are grown. The colonies are replica-plated onto nitrocellulose filters and screened by the assay method described Example 7. Colonies which exhibit dark staining with the rabbit polyclonal antibodies will contain plasmids which complement the mnn1 mutation and allow the host cell to make wild-type glycosylated proteins. Plasmid DNA is isolated from the positive clones by methods known in the literature (e.g., Hartig et al., ibid.) and is transformed into E. coli transformants. Plasmid DNA is isolated from E. Coli transformants and is subjected to restriction enzyme analysis.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. A method for producing a heterologous protein or polypeptide, comprising:
   introducing into a yeast cell carrying a defect in a gene whose product is required for the addition of outer chain oligosaccharide moieties to glycoproteins a first DNA construct comprising a regulated promoter followed downstream by a DNA sequence which complements said defect;
   introducing into said cell a second DNA construct comprising a second promoter followed downstream by a DNA sequence encoding a secretion signal and a DNA sequence encoding a heterologous protein or polypeptide;

culturing the cell under a first set of growth conditions such that the DNA sequence which complements said defect is expressed;

culturing the cell under a second set of growth conditions such that the DNA sequence which complements said defect is not expressed and the DNA sequence encoding the heterologous protein or polypeptide is expressed; and isolating the heterologous protein or polypeptide.

2. The method of claim 1 wherein said cell is a Saccharomyces spp. cell or a Schizosaccharomyces spp. cell.

3. The method of claim 2 wherein said cell is a *Saccharomyces cerevisiae* cell.

4. The method of claim 3 wherein said gene is selected from the group consisting of the MNN7, MNN8, MNN9 and MNN10 genes.

5. The method of claim 4 wherein said cell further carries a defect in the MNN1 gene.

6. The method of claim 3 wherein said cell contains a conditional mutation in a gene required for the expression of silent mating-type loci and the regulated promoter comprises a mating-type regulatory element.

7. The method of claim 6 wherein the conditional mutation is the sir3-8 mutation.

8. The method of claim 6 wherein the regulated promoter further comprises the TPI1 promoter.

9. The method of claim 3 wherein said secretion signal is selected from the group consisting of the MFα1 pre-pro sequence, the PHO5 secretion signal, the SUC2 secretion signal and the BAR1 secretion signal.

10. The method of claim 1 wherein said second promoter is a regulated promoter.

11. The method of claim 1 wherein said first and second DNA constructs are introduced into the yeast cell on a single plasmid.

12. The method of claim 1 wherein said defect is a point mutation.

13. The method of claim 1 wherein said defect is a genetic deletion.

14. The method of claim 1 wherein said protein or polypeptide is selected from the group consisting of tissue plasminogen activator, urokinase, immunoglobulins, platelet-derived growth factor, plasminogen, thrombin, factor XIII.

15. A yeast cell carrying a defect in a gene whose product is required for the addition of outer chain oligosaccharide moieties to glycoproteins, said cell transformed with a first DNA construct comprising a regulated promoter followed downstream by a DNA sequence with complements said defect, and a second DNA construct comprising a second promoter followed downstream by a DNA sequence encoding a secretion signal and a DNA sequence encoding a heterologous protein or polypeptide.

16. The yeast cell of claim 15 wherein said cell is a Saccharomyces spp. cell or a Schizosaccharomyces spp. cell.

17. The cell of claim 16 wherein said cell is a *Saccharomyces cerevisiae* cell.

18. The yeast cell of claim 17 wherein said gene is selected from the group consisting of the MNN7, MNN8, MNN9 and MNN10 genes.

19. The yeast cell of claim 18 wherein said cell further carries a defect in the MNN1 gene.

20. The yeast cell of claim 17 wherein said cell contains a conditional mutation in a gene required for the expression of silent mating-type loci and said regulated promoter comprises a mating-type regulatory element.

21. The yeast cell of claim 20 wherein the conditional mutation is the sir3-8 mutation.

22. The yeast cell of claim 20 wherein said regulated promoter further comprises the TPI1 promoter.

23. The yeast cell of claim 17 wherein said secretion signal is selected from the group consisting of the MFα1 pre-pro sequence, the PHO5 secretion signal, the SUC2 secretion signal and the BAR1 secretion signal.

24. The cell of claim 15 wherein said second promoter is a regulated promoter.

25. The cell of claim 15 wherein said first and second DNA constructs are contained on a single plasmid.

26. The cell of claim 15 wherein said first DNA construct is integrated into the genome of the cell.

27. The cell of claim 15 wherein said second DNA construct is integrated into the genome of the cell.

28. The cell of claim 15 wherein said defect is a point mutation.

29. The cell of claim 15 wherein said defect is a genetic deletion.

30. The cell of claim 15 wherein said protein or polypeptide is selected from the group consisting of tissue plasminogen activator, urokinase, immunoglobulins, platelet-derived growth factor, plasminogen, thrombin, factor XIII.

* * * * *